United States Patent
Vu et al.

(10) Patent No.: US 10,714,962 B2
(45) Date of Patent: Jul. 14, 2020

(54) POWER SUPPLYING DEVICE AND POWER RECEIVING/SUPPLYING DEVICE

(71) Applicant: NITTO DENKO CORPORATION, Ibaraki-shi, Osaka (JP)

(72) Inventors: Nam Tung Vu, Ibaraki (JP); Takezo Hatanaka, Ibaraki (JP); Taiki Sueyoshi, Ibaraki (JP); Masami Inoue, Ibaraki (JP); Hisashi Tsuda, Ibaraki (JP)

(73) Assignee: NITTO DENKO CORPORATION, Ibaraki-shi, Osaka (JP)

( * ) Notice: Subject to any disclaimer, the term of this patent is extended or adjusted under 35 U.S.C. 154(b) by 45 days.

(21) Appl. No.: 16/073,254

(22) PCT Filed: Jan. 26, 2017

(86) PCT No.: PCT/JP2017/002658
§ 371 (c)(1),
(2) Date: Jul. 26, 2018

(87) PCT Pub. No.: WO2017/131068
PCT Pub. Date: Mar. 8, 2017

(65) Prior Publication Data
US 2019/0044365 A1 Feb. 7, 2019

(30) Foreign Application Priority Data
Jan. 27, 2016 (JP) ................. 2016-013194

(51) Int. Cl.
*H02J 7/00* (2006.01)
*H02J 7/02* (2016.01)
(Continued)

(52) U.S. Cl.
CPC ............... *H02J 7/025* (2013.01); *A61L 2/06* (2013.01); *A61L 2/10* (2013.01); *A61L 2/26* (2013.01);
(Continued)

(58) Field of Classification Search
CPC .. H02J 7/025; H02J 50/10; H02J 50/12; H02J 50/50; H02J 7/00; H02J 7/0042;
(Continued)

(56) References Cited

U.S. PATENT DOCUMENTS

2009/0051327 A1 * 2/2009 Bohne ................. H02J 7/0004
320/162
2010/0141042 A1 6/2010 Kesler et al.
(Continued)

FOREIGN PATENT DOCUMENTS

EP 2161811 A1 3/2010
GB 2117579 A 10/1983
(Continued)

OTHER PUBLICATIONS

May 31, 2019 extended Search Report issued in European Patent Application No. 17744298.5.
(Continued)

*Primary Examiner* — Zixuan Zhou
(74) *Attorney, Agent, or Firm* — Oliff PLC

(57) ABSTRACT

A driving device is easily handled at the start and end of charging. A housing cup which includes a bottom surface portion on which at least one driving device including a power-receiving device is placed and a side face portion extending outward from the peripheral edge portion of the bottom surface portion and is formed so that an upper peripheral edge portion of the side face portion is an opening portion, and a magnetic field formation device which is configured to generate a variable magnetic field at a housing
(Continued)

region surrounded by the bottom surface portion and the side face portion to allow the power-receiving device to receive power irrespective of the direction and position of the power-receiving device are provided.

8 Claims, 20 Drawing Sheets

(51) Int. Cl.
| | |
|---|---|
| H02J 50/12 | (2016.01) |
| H01F 27/02 | (2006.01) |
| H02J 50/50 | (2016.01) |
| H02J 50/10 | (2016.01) |
| H01F 27/28 | (2006.01) |
| A61L 2/06 | (2006.01) |
| A61L 2/10 | (2006.01) |
| A61L 2/26 | (2006.01) |
| H01F 38/14 | (2006.01) |

(52) U.S. Cl.
CPC ......... *H01F 27/02* (2013.01); *H01F 27/2823* (2013.01); *H01F 38/14* (2013.01); *H02J 7/00* (2013.01); *H02J 7/0042* (2013.01); *H02J 7/0047* (2013.01); *H02J 50/10* (2016.02); *H02J 50/12* (2016.02); *H02J 50/50* (2016.02)

(58) Field of Classification Search
CPC .. H02J 7/0047; A61L 2/06; A61L 2/10; A61L 2/26; H01F 27/02; H01F 27/2823; H01F 38/14
USPC .......................................... 320/108; 307/104
See application file for complete search history.

(56) References Cited

U.S. PATENT DOCUMENTS

| | | | |
|---|---|---|---|
| 2010/0201189 A1 | 8/2010 | Kirby et al. | |
| 2011/0163714 A1* | 7/2011 | Ettes ................. | H02J 7/025 320/108 |
| 2015/0326061 A1 | 11/2015 | Davison et al. | |
| 2018/0193121 A1* | 7/2018 | Zhao ................. | A61C 17/221 |

FOREIGN PATENT DOCUMENTS

| | | |
|---|---|---|
| JP | 2003-189508 A | 7/2003 |
| JP | 2008-236886 A | 10/2008 |
| JP | 2012-502610 A | 1/2012 |
| JP | 2012-504387 A | 2/2012 |
| JP | 2012-517795 A | 8/2012 |
| WO | 2013/065277 A1 | 5/2013 |
| WO | 2013093697 A1 | 6/2013 |

OTHER PUBLICATIONS

Feb. 21, 2017 International Search Report issued in International Patent Application PCT/JP2017/002658.
Takahiro Nakata et al; "Expansion of Transmission Range by Using Nested Coil for Wireless Power Transfer via Magnetic Resonance Coupling"; Proceedings of the Society Conference of IEICE; Sep. 9, 2014; p. 438.
Jul. 31, 2018 International Preliminary Report on Patentability issued in International Patent Application No. PCT/JP2017/002658.
Mar. 3, 2020 Office Action issued in Japanese Patent Application No. 2016-013194.

* cited by examiner

COIL SURFACE DIRECTION

COIL SURFACE DIRECTION

INTERSECTION

FIG.11

POWER-SUPPLYING COIL SHORT-CIRCUIT MECHANISM

| | POWER-SUPPLYING COIL 111 | POWER-SUPPLYING COIL 112 | POWER-SUPPLYING COIL 113 |
|---|---|---|---|
| SHORT-CIRCUIT PATTERN 1 | ○ | × | × |
| SHORT-CIRCUIT PATTERN 2 | × | ○ | × |
| SHORT-CIRCUIT PATTERN 3 | × | × | ○ |
| SHORT-CIRCUIT PATTERN 4 | ○ | ○ | × |
| SHORT-CIRCUIT PATTERN 5 | × | ○ | ○ |
| SHORT-CIRCUIT PATTERN 6 | ○ | × | ○ |

| SHORT-CIRCUIT TIME | SHORT-CIRCUIT PATTERN |
|---|---|
| TIME 1 | EVERY 1 PATTERN |
| TIME 2 | EVERY 2 PATTERNS |
| TIME 3 | EVERY 3 PATTERNS |
| ... | ... |
| TIME n | EVERY n PATTERNS |

CURRENT PATH SWITCHER

| | ROUTE A | ROUTE B | ROUTE C |
|---|---|---|---|
| CONNECTION PATTERN 1 | ○ | × | × |
| CONNECTION PATTERN 2 | × | ○ | × |
| CONNECTION PATTERN 3 | × | × | ○ |
| CONNECTION PATTERN 4 | ○ | ○ | × |
| CONNECTION PATTERN 5 | × | ○ | ○ |
| CONNECTION PATTERN 6 | ○ | × | ○ |

| PAUSE TIME | PAUSE PATTERN |
|---|---|
| TIME 1 | EVERY 1 PATTERN |
| TIME 2 | EVERY 2 PATTERNS |
| TIME 3 | EVERY 3 PATTERNS |
| ... | ... |
| TIME n | EVERY n PATTERNS |

1311

POWER SUPPLYING DEVICE AND POWER RECEIVING/SUPPLYING DEVICE

TECHNICAL FIELD

The present invention relates to a power-supplying device performing wireless power supply and a power receiving/supplying device.

BACKGROUND

Various structures have been proposed as a power-supplying device performing wireless power supply. For example, Patent Literature 1 discloses that a positioning protrusion is formed on a charger, a positioning recess is formed in a mobile device which is an electronic device, and the mobile device is positioned with respect to the charger as the positioning protrusion is fitted with the positioning recess, so that charging is performed in a wireless manner.

CITATION LIST

Patent Literature

[Patent Literature 1] Japanese Unexamined Patent Publication No. 2008-236886

SUMMARY OF INVENTION

Technical Problem

However, the structure recited in Patent Literature 1 is disadvantageous in that, because an operation to fit the positioning recess of the mobile device with the positioning protrusion of the power-supplying device and an operation to cancel the fitting are required at the start and the end of the charging, handling of the mobile device is difficult at the start and the end of the charging.

An object of the present invention is therefore to provide a power-supplying device and a power receiving/supplying device, in which a driving device which encompasses a mobile device is easily handled at the start and end of charging.

Solution to Problem

The present invention provides a power-supplying device including: a housing cup which includes a bottom surface portion on which at least one driving device including a power-receiving device is placed and a side face portion extending outward from a peripheral edge portion of the bottom surface portion, the housing cup being formed so that an upper peripheral edge portion of the side face portion is an opening portion; and a magnetic field formation device configured to generate a variable magnetic field at a housing region surrounded by the bottom surface portion and the side face portion to allow the power-receiving device to receive power irrespective of the direction and position of the power-receiving device.

According to this arrangement, when, for example, the side face portion of the housing cup is inclined to allow a driving device to slidingly move by its own weight to a central portion of the bottom surface portion, the width of the bottom surface portion is restricted for the reason that the inclination angle must be sufficient to allow the driving device to slide down. In this regard, the arrangement above allows the bottom surface portion to be large enough to reach a region where a variable magnetic field is generated by the magnetic field formation device. Furthermore, because the housing cup with a long opening diameter is obtained, handling of the driving device at the start and end of the charging, e.g., a housing operation and a takeout operation, are easily done.

The magnetic field formation device of the present invention may repeatedly change plural magnetic field states each of which is a combination of the direction, density, and magnitude of magnetic lines of force in the variable magnetic field.

According to this arrangement, because the magnetic field strength of the variable magnetic field at the housing region is repeatedly changeable by repeatedly changing the magnetic field states each of which is a combination of the direction, density, and magnitude of magnetic lines of force in the variable magnetic field, power supply can be done without significant deterioration in the power receiving efficiency depending on the direction and position of the power-receiving device.

The power-supplying device of the present invention may be arranged such that the magnetic field formation device includes: power-supplying coils each of which generates a variable magnetic field as a variable current is supplied to each of the power-supplying coils via a first current path on one coil end side and a second current path on the other coil end side; a resonance capacitor which is provided on at least one of the first current path and the second current path; and a power-supplying coil short-circuit mechanism which is capable of causing at least one of the power-supplying coils to function as a power supplying resonator by short-circuiting end portions of the first current path and the second current path.

According to the arrangement above, when the end portions of the first current path and the second current path of at least one of the power-supplying coils are short-circuited by the power-supplying coil short-circuit mechanism, this power-supplying coil functions as a power supplying resonator which resonates with a variable magnetic field generated by the other power-supplying coil to which a variable current is supplied. In this way, a variable magnetic field in which the power-supplying coil and the power supplying resonator exist is generated only by the power-supplying coils.

The power-supplying device of the present invention may be arranged such that the magnetic field formation device generates a variable magnetic field at a predetermined region, all of the power-supplying coils are disposed so that coil surfaces oppose the predetermined region, and at least one of the power-supplying coils is disposed to have a coil surface direction which intersects with coil surface directions of the other power-supplying coils. The power-supplying device of the present invention may be arranged such that the magnetic field formation device generates a variable magnetic field at a predetermined region, all of the power-supplying coils are disposed so that coil surfaces oppose the predetermined region, and at least one of the power-supplying coils is disposed to have a coil surface direction which is parallel to coil surface directions of the other power-supplying coils.

According to the arrangements above, a variable magnetic field with high magnetic field strength or low magnetic field strength can be formed at a part of the predetermined region by the variable magnetic field of the power-supplying coil and the variable magnetic field of the power-supplying coil functioning as a power supplying resonator, based on the positional relation between the power-supplying coils. This is achieved by adjusting the angles, locations, etc. of the coil surfaces of the power-supplying coils.

The power-supplying device of the present invention may further include a current output controller which is configured to output a variable current to one of output targets which are at least one of and not all of the power-supplying coils and to be capable of switching the output target to which the variable current is output.

According to this arrangement, it is possible to change the distribution of the magnetic field strength of a variable magnetic field by sending a magnetic field from each power-supplying coil to the power-supplying coil functioning as the power supplying resonator at a different angle. Furthermore, as the power supplying resonator (power-supplying coil) resonates on account of the variable magnetic field of each of the power-supplying coils, the magnetic field strength of the variable magnetic field at the predetermined region is enhanced.

The power-supplying device of the present invention may be arranged such that the current output controller executes a stop process of not outputting the variable current to any of the power-supplying coils, with a predetermined combination of a timing and a duration.

With this arrangement, it is possible to easily generate a variable magnetic field with predetermined magnetic field strength in consideration of heat generation and power consumption, by adjusting the timing and duration of the stop process.

The magnetic field formation device of the present invention may include: at least one power supplying resonator configured to generate the variable magnetic field; and power-supplying coils configured to generate an induced current in the at least one power supplying resonator, the at least one power supplying resonator and the power-supplying coils may be disposed so that coil surfaces oppose a predetermined region including the housing region surrounded by the bottom surface portion and the side face portion of the housing cup, and at least one of the power-supplying coils may be disposed to have a coil surface direction which intersects with coil surface directions of the other power-supplying coils. The magnetic field formation device of the present invention may include: at least one power supplying resonator configured to generate the variable magnetic field; and power-supplying coils configured to generate an induced current in the at least one power supplying resonator, the at least one power supplying resonator and the power-supplying coils may be disposed so that coil surfaces oppose a predetermined region including the housing region surrounded by the bottom surface portion and the side face portion of the housing cup, and at least one of the power-supplying coils may be disposed to have a coil surface direction which is parallel to coil surface directions of the other power-supplying coils.

According to the arrangements above, a variable magnetic field with high magnetic field strength or low magnetic field strength can be formed at a part of the predetermined region by the variable magnetic fields of the power-supplying coils and the variable magnetic field of the power supplying resonator, based on the positional relation between the power-supplying coils and the power supplying resonator. This is achieved by adjusting the angles, locations, etc. of the coil surfaces of the power-supplying coils.

The power-supplying device of the present invention may further include a display which is configured to display a charging state of a battery provided in the driving device, a drier configured to dry the driving device, and a sterilizer configured to sterilize the driving device.

According to the present invention, a power receiving/supplying device includes: any one of the power-supplying devices described above; and a power-receiving device which is housed in the housing region of the housing cup of the power-supplying device and is configured to receive power by the variable magnetic field.

Advantageous Effects of Invention

According to the present invention, driving device is easily handled at the start and end of charging.

BRIEF DESCRIPTION OF DRAWINGS

FIG. 11 illustrates operations of a power-supplying coil short-circuit mechanism.

FIG. 13 is an explanatory diagram of operations of a current path switcher.

DESCRIPTION OF EMBODIMENTS

Embodiment 1

The following will describe an embodiment of the present invention with reference to FIG. 1 to FIG. 17. (Power Supplying Device)

Figure 1:
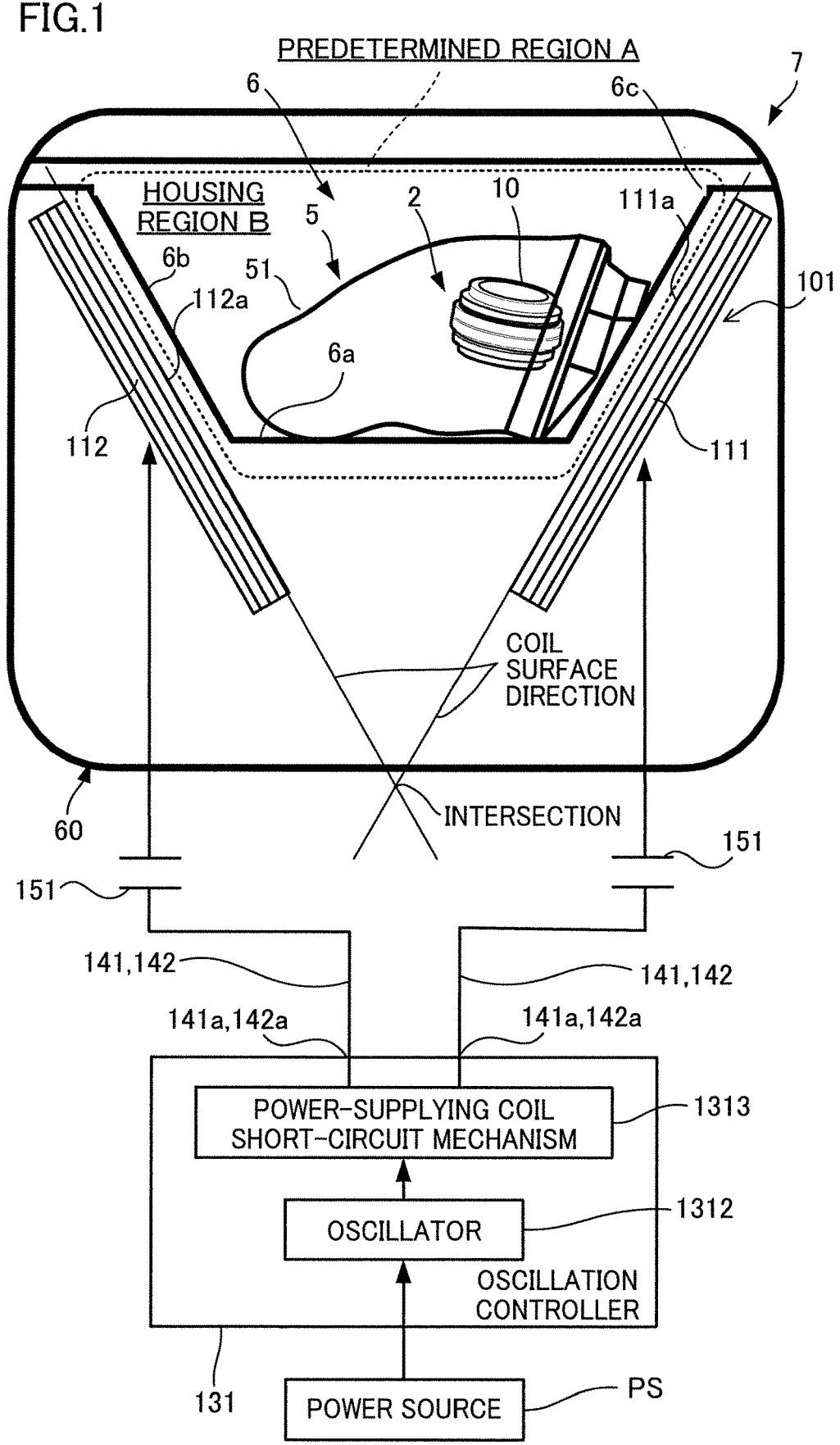
FIG. 1 is a schematic explanatory diagram of a charger in a front view.

As shown in FIG. 1, a charger 7 which is a power-supplying device includes: a housing cup 6 having a housing region B; and a magnetic field formation device 101 configured to generate a variable magnetic field at a predetermined region A including the housing region B. The housing cup 6 is provided in a charging case 60. The housing cup 6 includes a bottom surface portion 6a on which at least one driving device 5 including a power-receiving device is placed and a side face portion 6b extending outward from the peripheral edge portion of the bottom surface portion 6a, and the housing cup 6 is formed so that an upper peripheral edge portion 6c of the side face portion 6b is an opening portion. The magnetic field formation device 101 is formed to generate a variable magnetic field at the housing region B surrounded by the bottom surface portion 6a and the side face portion 6b of the housing cup 6 to allow the driving device 5 to receive power irrespective of the direction and position of the driving device 5.

When, for example, the side face portion of the housing cup 6 is inclined to allow a driving device 5 to slidingly move by its own weight to a central portion of the bottom surface portion 6a, the width of the bottom surface portion 6a is restricted for the reason that the inclination angle must be sufficient to allow the driving device 5 to slide down. In this regard, the arrangement above allows the bottom surface portion 6a to be large enough to reach a region where a variable magnetic field is generated by the magnetic field formation device 101. Furthermore, because the housing cup 6 with a long opening diameter is obtained, handling of the driving device 5 at the start and end of the charging, e.g., a housing operation and a takeout operation, are easily done. The driving device will be detailed later.

The magnetic field formation device 101 may be arranged to repeatedly change plural magnetic field states each of which is a combination of the direction, density, and magnitude of magnetic lines of force in a variable magnetic field. In this case, because the magnetic field strength of the variable magnetic field at the housing region is repeatedly changeable by repeatedly changing the magnetic field state which is a combination of the direction, density, and magnitude of magnetic lines of force in the variable magnetic field, power supply can be done without significant deterioration in the power receiving efficiency depending on the direction and position of the power-receiving device.

The magnetic field formation device 101 may be arranged to repeatedly change plural magnetic field states of generating a low magnetic field strength and a high magnetic field strength in one particular region. In this case, power supply with a magnetic field strength which is an average of the low magnetic field strength and the high magnetic field strength is possible in the particular region.

The magnetic field formation device 101 may include plural magnetic field generation sources (power-supplying coils or power-supplying resonators) provided at different locations around the housing cup 6, and may be able to change plural magnetic field states which are combinations of variable magnetic fields generated by these magnetic field generation sources. Alternatively, the magnetic field formation device 101 may include plural magnetic field generation sources (power-supplying coils or power-supplying resonators) provided in different directions around the housing cup 6, and may change plural magnetic field states which are combinations of variable magnetic fields generated by these magnetic field generation sources, in order to try to uniformize the distribution of the magnetic field strength in the housing region B.

(Power Supplying Device: Housing Cup)

Figure 2:
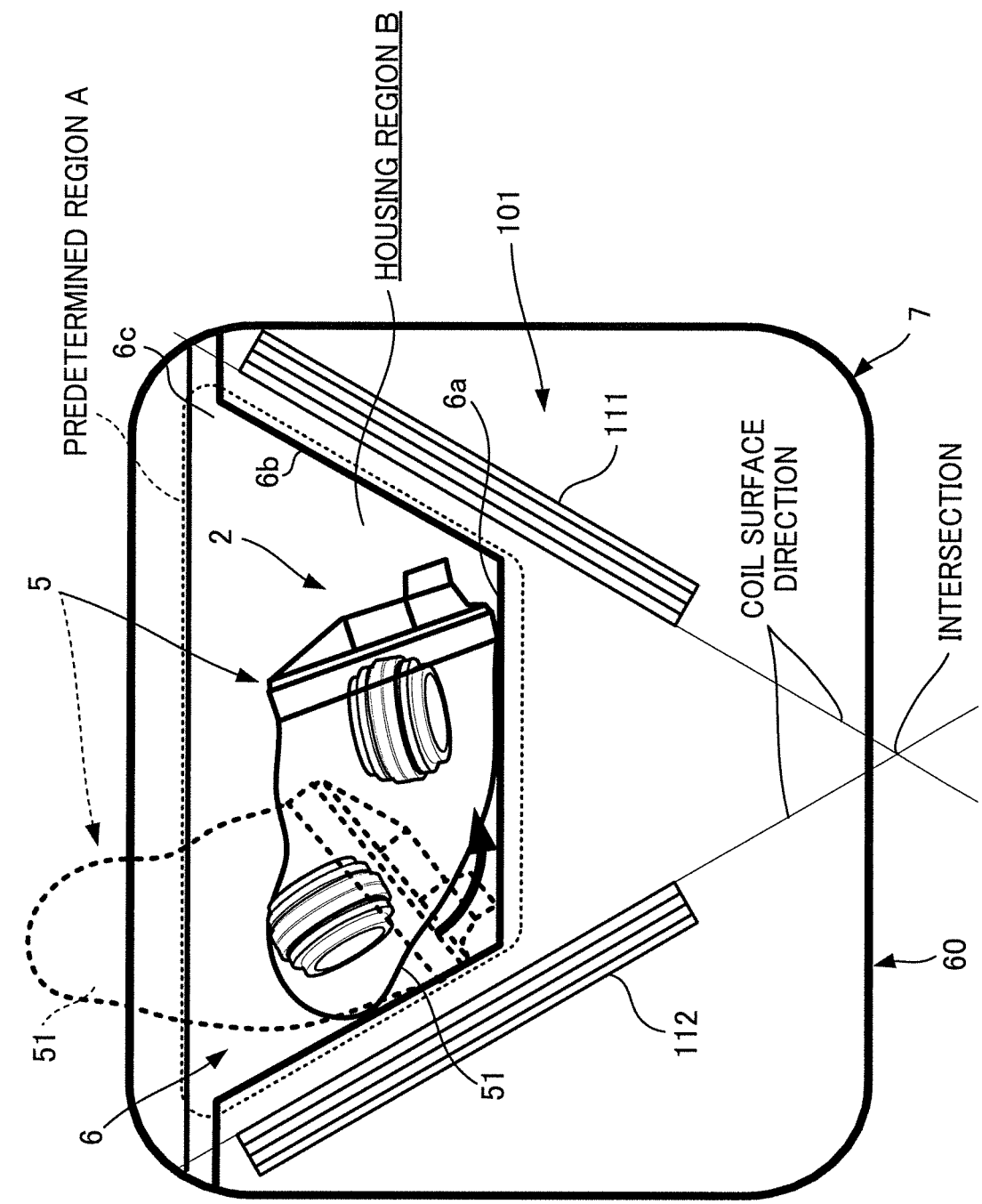
FIG. 2 illustrates an operation state of a driving device housed in a charger.

As shown in FIG. 2, the bottom surface portion 6a of the housing cup 6 may be flat, may be curved to convex or concave, or may have plural concave portions or protrusions at a flat surface or a curved surface. The bottom surface portion 6a may be horizontally disposed or inclined with respect to the horizontal plane. The inclination angle of the side face portion 6b of the housing cup 6 is preferably set to allow the driving device 5 to slidingly move by its own weight to the bottom surface portion 6a while the side face portion 6b is in contact with a casing 51 of the driving device 5. This improves the handling when the driving device 5 is placed at the housing region B of the housing cup 6. Each of the bottom surface portion 6a and the side face portion 6b of the housing cup 6 may have one or more opening portion. In this case, as hot air, ultraviolet light, etc. is sent from a drier or a sterilizing device to the housing region B through the opening portion, the driving device 5 can be dried or sterilized by the hot air, ultraviolet light, etc., while being charged.

The minimum length of a line segment passing the center of the bottom surface portion 6a of the housing cup 6 is preferably longer than the maximum length of the driving device 5. In this case, because the driving device 5 can be mounted in a horizontal manner such that a side face of the driving device 5 is in contact with the bottom surface portion 6a, the positional relation in the height direction between the driving device 5 and the bottom surface portion 6a of the power-receiving device is stable as compared to cases where the driving device 5 is mounted in a vertical manner and leans on the side face portion 6b. It is therefore easy to design the power supply to the driving device 5.

The bottom surface portion 6a and the side face portion 6b of the housing cup 6 preferably have a large number of concaves and convexes in order to decrease the contact area with the driving device 5. In this case, the maximum static friction coefficient of the bottom surface portion 6a and the side face portion 6b can be easily decreased. In order to improve the slipperiness with the driving device 5, the bottom surface portion 6a and the side face portion 6b are preferably arranged so that a contact layer formed by fluorine coating (Teflon (registered trademark)), glass coating, etc. which improves the smoothness is laminated on a base of the housing cup 6. Each of the bottom surface portion 6a and the side face portion 6b may be a combination of a stacked structure of a contact layer and a rough surface, or at least one of the bottom surface portion 6a and the side face portion 6b may be a combination of a stacked structure of a contact layer and a rough surface. Alternatively, a contact layer may be formed in one of the bottom surface portion 6a and the side face portion 6b whereas a rough surface may be formed on the other one of the bottom surface portion 6a and the side face portion 6b.

Figure 3:
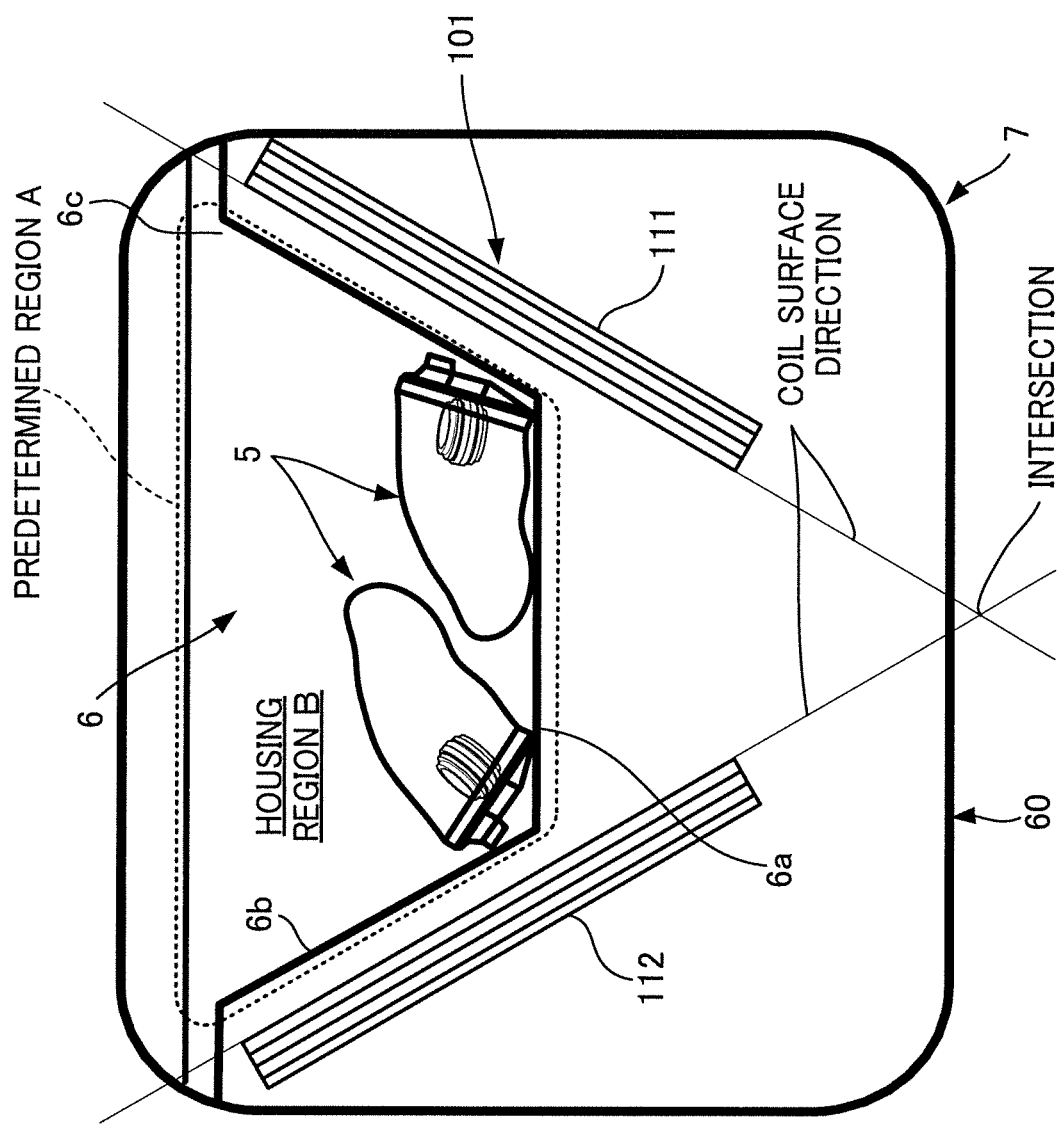
FIG. 3 illustrates a state of the driving device housed in the charger.

As shown in FIG. 3, the housing cup 6 may be arranged such that plural driving devices 5 which are identical or different in size or type are simultaneously placed at the housing region B. To put it differently, the housing region B of the housing cup 6 may have a capacity capable of simultaneously storing plural driving devices 5 which are identical or different in size or type.

Figure 4:
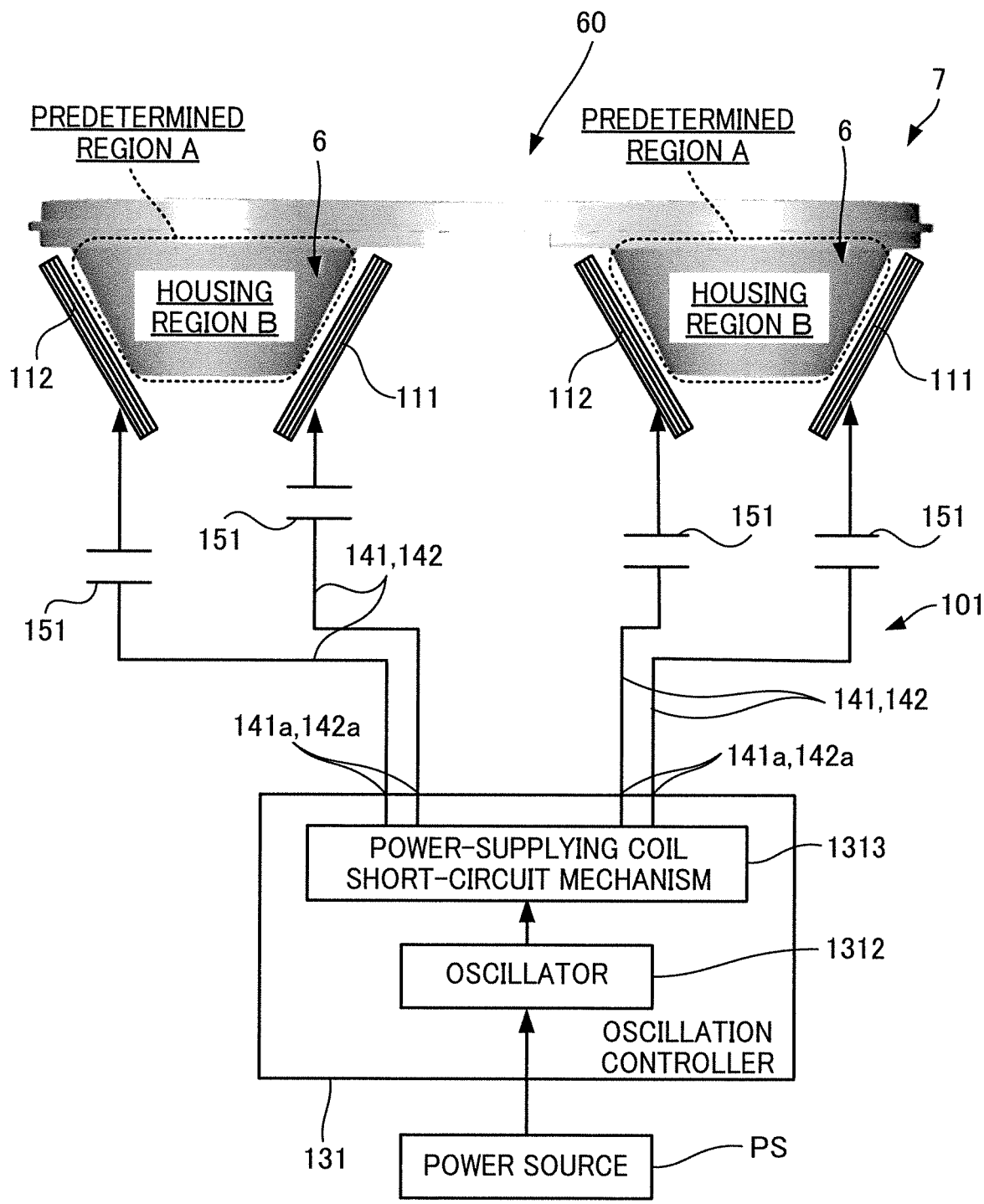
FIG. 4 is a schematic explanatory diagram of a charger in a front view.

As shown in FIG. 4, the charging case 60 may have plural housing regions B on account of inclusion of plural housing cups 6. In this case, for example, hearing aids for the left and right ears can be stored as the driving devices 5 in the respective housing regions B of the housing cups 6. Alternatively, for example, a hearing aid is housed in one housing cup 6 (housing region B) whereas a mobile phone or the like is housed in the other housing cup 6 (housing region B). In this way, different driving devices 5 can be sorted and charged by one charger 7.

(Power Supplying Device: Magnetic Field Formation Device)

As shown in FIG. 1, the magnetic field formation device 101 mounted on the charger 7 is provided to generate a variable magnetic field at the predetermined region A including the housing region B. To be more specific, the magnetic field formation device 101 includes: power-supplying coils 111 and 112 each of which generates a variable magnetic field due to the supply of a variable current via a first current path 141 on one coil end 141a side and a second current path 142 on the other coil end 142a side; resonance capacitors 151 and 151 which are provided on the first current path 141 and the second current path 142; and a power-supplying coil short-circuit mechanism 1313 which is able to cause at least one of the power-supplying coils 111 and 112 to function as a power supplying resonator by allowing the end portions 141a and 142a of the first current path 141 and the second current path 142 to short-circuit with each other.

Each resonance capacitor 151 is provided on the first current path 141 or the second current path 142 to be in series with or parallel to one of the power-supplying coils 111 and 112. Specific examples are shown in FIG. 5A to FIG. 5H.

Figure 5A:
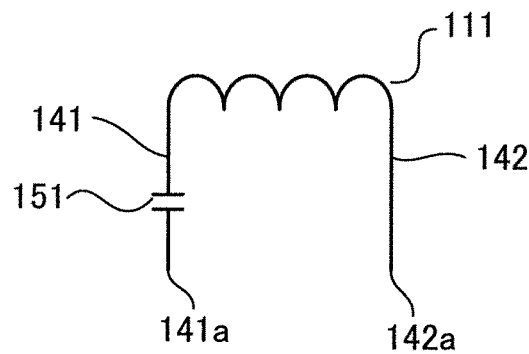
FIG. 5A illustrates a connection relation between a power-supplying coil and a resonance capacitor.
Figure 5B:
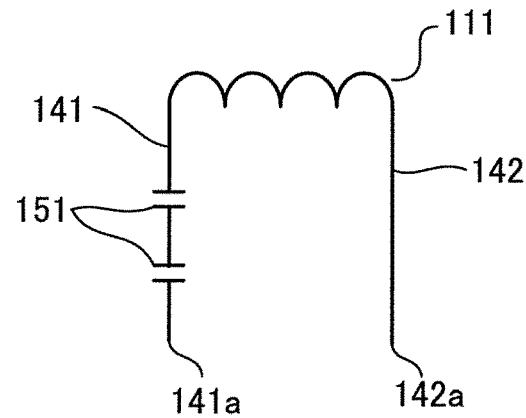
FIG. 5B illustrates a connection relation between a power-supplying coil and a resonance capacitor.
Figure 5C:
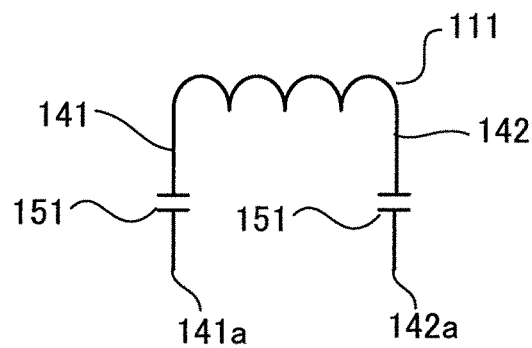
FIG. 5C illustrates a connection relation between a power-supplying coil and a resonance capacitor.

FIG. 5A shows a state in which a resonance capacitor 151 is connected in series at a part of the first current path 141, which is between the end portion 141a of the first current path 141 and the coil end of the power-supplying coil 111. FIG. 5B shows a state in which two resonance capacitors 151 are connected in series on the first current path 141. FIG. 5C shows a state in which resonance capacitors 151 are connected in series on the first current path 141 and the second current path 142, respectively.

Figure 5D:
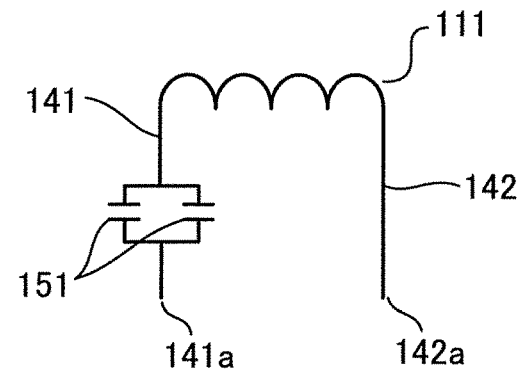
FIG. 5D illustrates a connection relation between a power-supplying coil and a resonance capacitor.
Figure 5E:
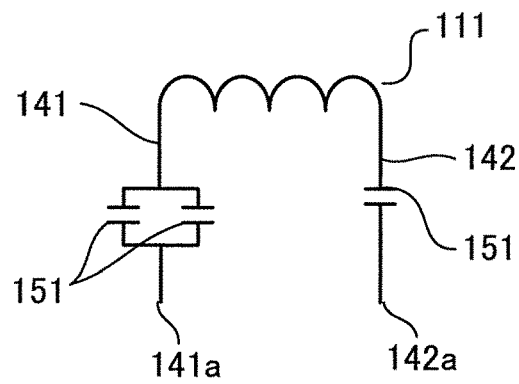
FIG. 5E illustrates a connection relation between a power-supplying coil and a resonance capacitor.
Figure 5F:
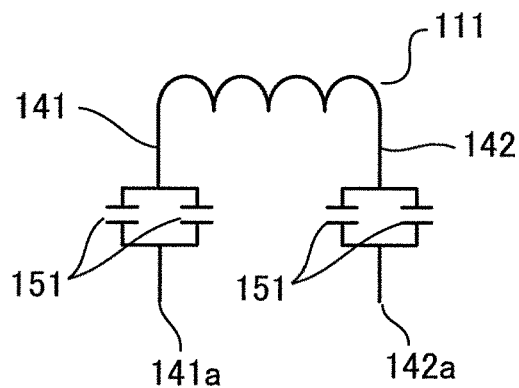
FIG. 5F illustrates a connection relation between a power-supplying coil and a resonance capacitor.

FIG. 5D shows a state in which two resonance capacitors 151 provided in a parallel manner are connected in series on the first current path 141. FIG. 5E shows a state in which two resonance capacitors 151 provided in a parallel manner are connected in series on the first current path 141 whereas a resonance capacitor 151 is connected in series on the second current path 142. FIG. 5F shows a state in which two resonance capacitors 151 provided in a parallel manner are connected in series on the first current path 141 whereas two resonance capacitors 151 provided in a parallel manner are connected in series on the second current path 142.

Figure 5G:
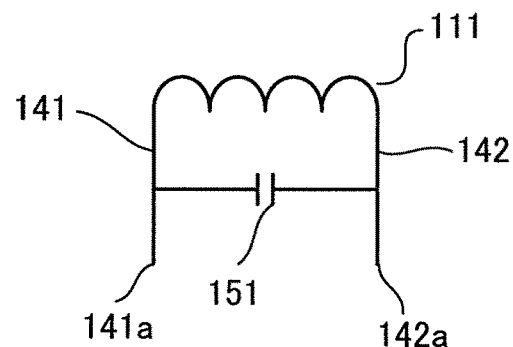
FIG. 5G illustrates a connection relation between a power-supplying coil and a resonance capacitor.
Figure 5H:
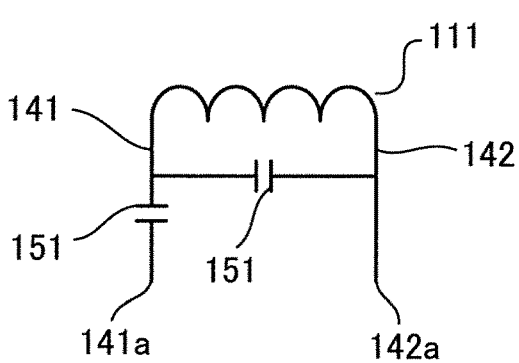
FIG. 5H illustrates a connection relation between a power-supplying coil and a resonance capacitor.

FIG. 5G shows a state in which a resonance capacitor 151 is connected to the first current path 141 and the second current path 142 to be parallel to the power-supplying coil 111. FIG. 5H shows a state in which a resonance capacitor 151 is connected to the first current path 141 and the second current path 142 to be parallel to the power-supplying coil 111, and a resonance capacitor 151 is connected in series on the first current path 141. The connection states shown in FIG. 5A to FIG. 5H are examples, and the number, the series connection, the parallel connection, and the locations of the resonance capacitors 151 may be suitably selected and combined.

As shown in FIG. 1, the power-supplying coil short-circuit mechanism 1313 is provided in an oscillation controller 131 together with an oscillator 1312. The oscillation controller 131 will be detailed later. With this arrangement, the magnetic field formation device 101 realizes a magnetic field formation method of switching at least one of the power-supplying coils 111 and 112 generating a variable magnetic field with the supply of a variable current to a power supplying resonator by short-circuiting the end portions 141a and 142a of the first current path 141 and the second current path 142 with each other.

In the magnetic field formation device 101 structured as described above, when the end portions 141a and 142a of the first current path 141 and the second current path 142 of at least one of the power-supplying coils 111 and 112 are short-circuited by the power-supplying coil short-circuit mechanism 1313, this power-supplying coil 111 (112) functions as a power supplying resonator which resonates with a variable magnetic field generated by the other power-supplying coil 112 (111) to which a variable current is supplied. In this way, a variable magnetic field in which the power-supplying coil 111 (112) and the power supplying resonator 112 (111) exist is generated only by the power-supplying coils 111 and 112.

All of the power-supplying coils 111 and 112 are provided so that coil surfaces 111a and 112a oppose the predetermined region A, and at least one of the power-supplying coils 111 and 112 is provided to have a coil surface direction intersecting with the coil surface direction of the other one of the power-supplying coils 111 and 112. The coil surface direction is a direction in parallel to a coil surface.

Figure 6A:
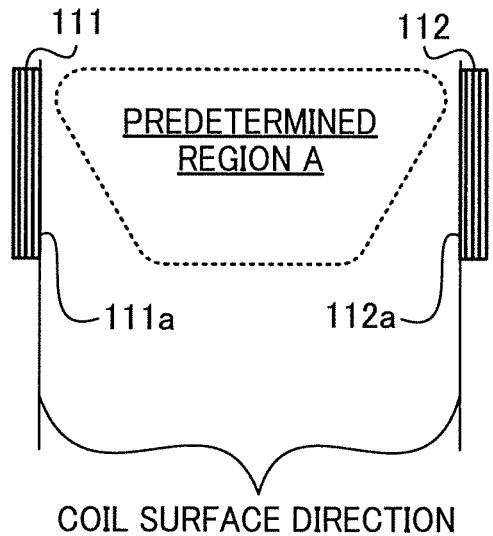
FIG. 6A is a schematic explanatory diagram of a magnetic field formation device in a front view.

Alternatively, as shown in FIG. 6A, at least one of the power-supplying coils 111 and 112 may be provided to have a coil surface direction parallel to the coil surface direction of the other one of the power-supplying coils 111 and 112. In this case, the power-supplying coils 111 and 112 may be arranged so that the coil surfaces 111a and 112a having the coil surface directions parallel to each other sandwich at least a part of the predetermined region A. Furthermore, in the case above, the power-supplying coils 111 and 112 may be disposed to at least partially overlap each other when one of the coil surfaces 111a and 112a having the coil surface directions parallel to each other is projected onto the other coil surface in the direction along the coil axis.

Alternatively, the power-supplying coils 111 and 112 may be disposed so that the coil surface 111a or 112a of at least one of the power-supplying coils 111 and 112 and the coil surface 111a or 112a of the other one of the power-supplying coils 111 and 112 are not on the same plane.

In the magnetic field formation device 101 structured as above, a variable magnetic field with high magnetic field strength or low magnetic field strength can be formed at a part of the predetermined region A by the variable magnetic field of the power-supplying coil 111 (112) and the variable magnetic field of the power-supplying coil 112 (111) functioning as a power supplying resonator, based on the positional relation between the power-supplying coils 111 and 112. This is achieved by adjusting the angles, locations, etc. of the coil surfaces 111a and 112a of the power-supplying coils 111 and 112. In this way, a magnetic field which is partially a variable magnetic field with high or low magnetic field strength can be formed at the predetermined region A.

Furthermore, in the magnetic field formation device 101, by the power-supplying coil 111 (112) functioning as a power supplying resonator and the other power-supplying coil 112 (111), a magnetic field area which enables power transmission by magnetic field resonance and a magnetic field area which enables power transmission by electromagnetic induction can be provided in the predetermined region. In other words, in the magnetic field formation device 101, because the distance in which the magnetic field resonance is possible is longer than the distance in which the electromagnetic induction is possible, a magnetic field area in which power transmission is mainly conducted by the electromagnetic induction in short distances from the power-supplying coil 111 (112) and a magnetic field area in which power transmission is conducted mainly by the magnetic field resonance in long distances can be provided in the predetermined region. On this account, the magnetic field formation device 101 is suitable for power transmission in a large-sized predetermined region.

The "variable magnetic field" indicates one of (1) a magnetic field in a state in which the direction of the magnetic lines of force alternately changes between the forward direction and the reverse direction, (2) a magnetic field in a state in which the magnetic field strength changes while the direction of the magnetic lines of force is the forward direction, (3) a magnetic field in a state in which the magnetic field strength changes while the direction of the magnetic lines of force is the reverse direction, and (4) a magnetic field in a state in which two or more of the states (1) to (3) are combined.

The "predetermined region A" may be of any size or shape. The predetermined region A is a reverse frustum in shape, in which the lower face is smaller than the upper face. The reverse frustum shape may be a reverse circular frustum shape, a reverse square frustum shape, or an N-sided frustum shape. While in the present embodiment the predetermined region A is reverse frustum in shape, the disclosure is not limited to this arrangement. In other words, the inclination angle of at least one side face may be different from the inclination angles of the remaining side faces in the predetermined region A, or the predetermined region A may be a hexahedron such as a rectangular parallelepiped body, a cube, or a triangular prism.

(Power Supplying Device: Magnetic Field Formation Device: Power-Supplying Coil)

The "power-supplying coils 111 and 112" are of a spiral type, a solenoid type, or a loop type, for example, and are coils which generate an induction current at a power-supplying coil 111 or 112 which functions as a power supplying resonator on account of an externally-supplied variable current. The "variable current" indicates one of (1) a current which alternately varies to the positive side and the negative side over 0 ampere, (2) a current which varies on the positive side, (3) a current which varies on the negative side, and (4) a current in a state in which two or more of the states (1) to (3) are combined.

All of the power-supplying coils 111 and 112 are provided so that coil surfaces 111a and 112a oppose the predetermined region A, and at least one of the power-supplying coils 111 and 112 is provided to have a coil surface direction intersecting with the coil surface direction of the other one of the power-supplying coils 111 and 112. On this account, the power-supplying coils 111 and 112 are disposed along the side faces of the predetermined region A and hence the coil surface directions intersect with each other at a location below the predetermined region A.

Figure 6B:
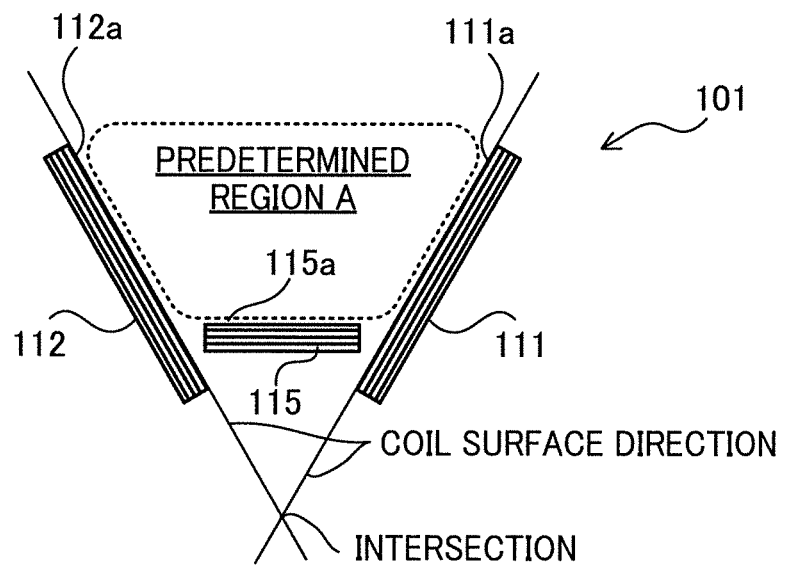
FIG. 6B is a schematic explanatory diagram of a magnetic field formation device in a front view.

While in the present embodiment two power-supplying coils 111 and 112 are provided for convenience of explanation, the number of the power-supplying coils is not limited to this. The number of the power-supplying coils may be variously set on condition that the number is two or more. For example, as shown in FIG. 6B, three power-supplying coils 111, 112, and 115 are provided, and a coil surface 115a of the power-supplying coil 115 is disposed to oppose the bottom surface of the predetermined region A.

Figure 7:
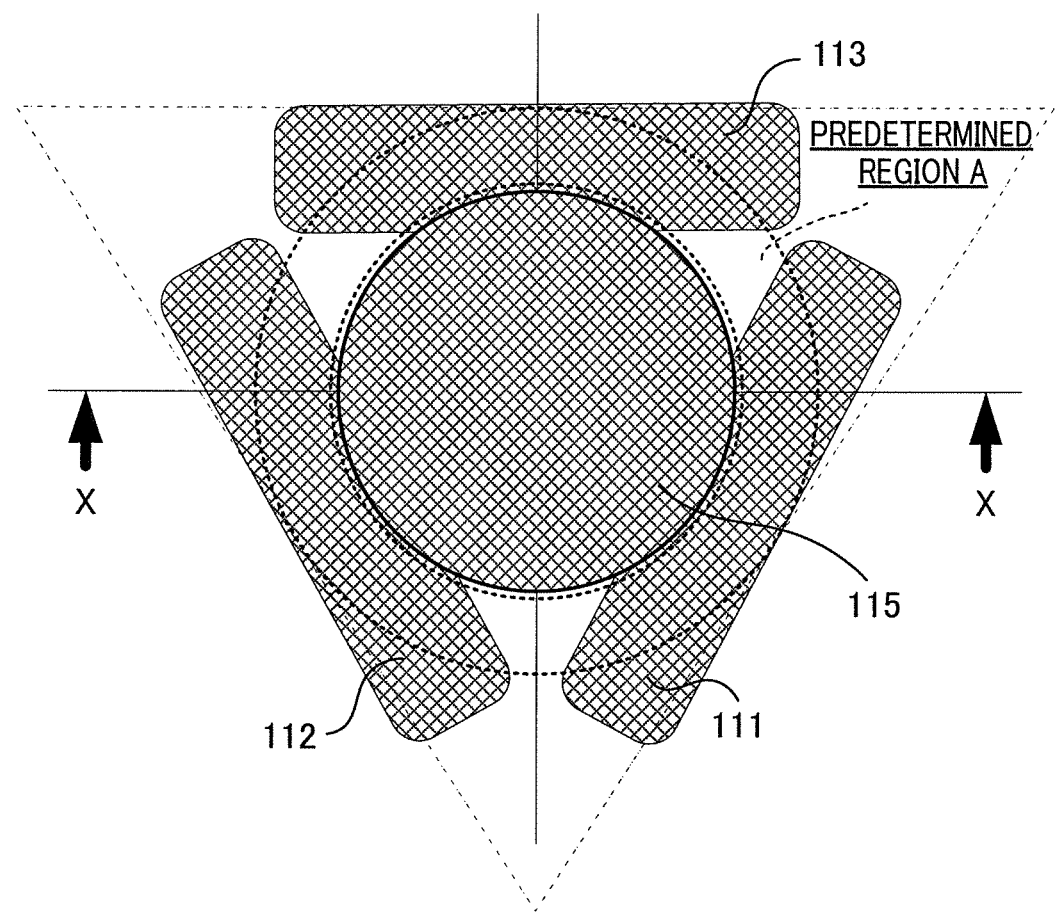
FIG. 7 is a schematic explanatory diagram of a magnetic field formation device in a plan view.

Alternatively, for example, as shown in FIG. 7, when viewed from a point above the predetermined region A, three power-supplying coils 111, 112, and 113 may be provided along the respective sides of an equilateral triangle which is centered at the predetermined region A. In this case, the state of the end face cut along the X-X line in FIG. 7 corresponds to the positional relation between the power-supplying coils 111, 112, and 115 shown in FIG. 6B.

Figure 8:
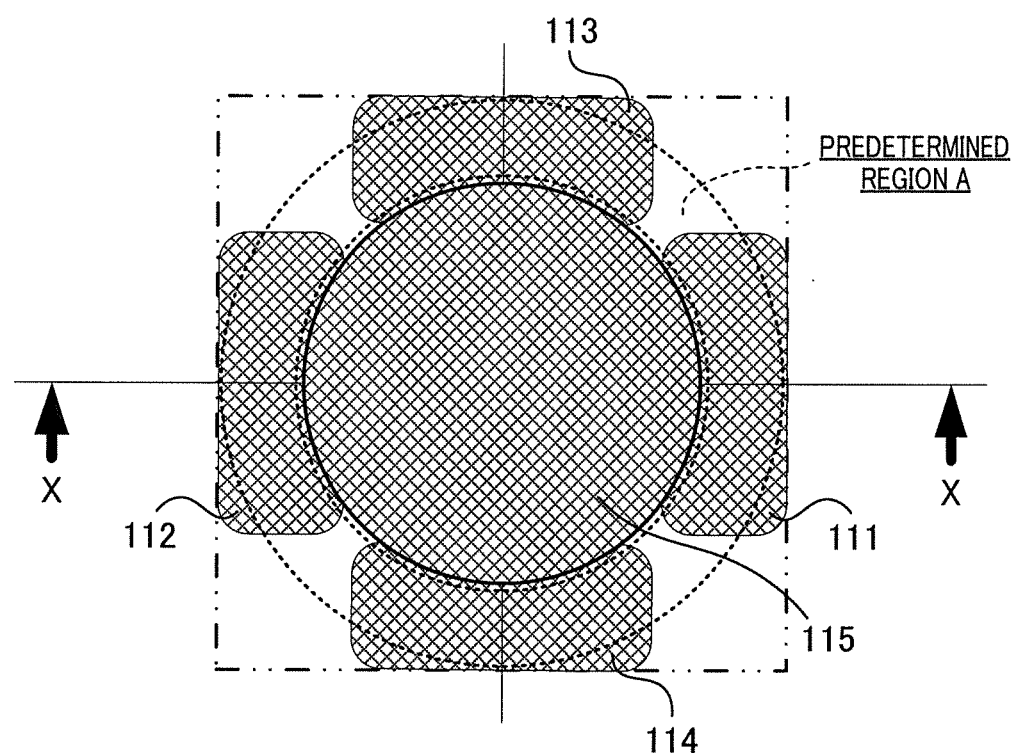
FIG. 8 is a schematic explanatory diagram of a magnetic field formation device in a plan view.

Alternatively, for example, as shown in FIG. 8, when viewed from a point above the predetermined region A, four power-supplying coils 111, 112, 113, and 114 may be provided along the respective sides of a square which is centered at the predetermined region A. In this case, the state of the end face cut along the X-X line in FIG. 8 corresponds to the positional relation between the power-supplying coils 111, 112, and 115 shown in FIG. 6B.

Figure 9:
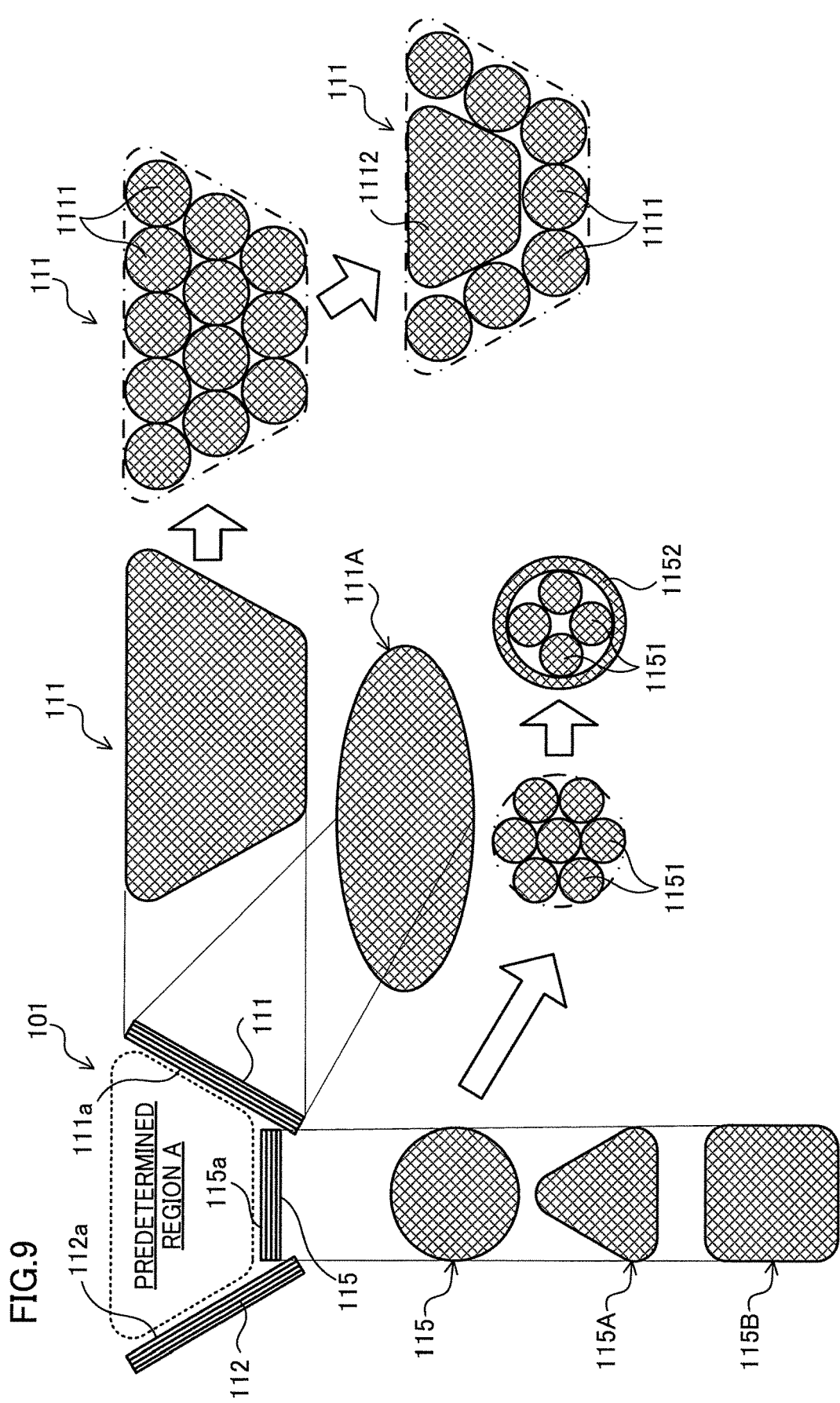
FIG. 9 is a schematic explanatory diagram of a magnetic field formation device in a front view.

As shown in FIG. 9, the coil surfaces of the power-supplying coils 111 and 112 provided to sandwich the predetermined region A have sizes and shapes corresponding to those of the side faces of the predetermined region A. For example, the coil surfaces 111a and 112a of the power-supplying coils 111 and 112 may be formed to be trapezoidal to correspond to the predetermined region A having a reverse frustum shape, or to be elliptical (power-supplying coil 111A). Each of the coil surfaces of the power-supplying coils 111 and 112 may be, for example, circular, triangular, quadrangular, or polygonal in shape to correspond to the size of the predetermined region A. The shapes of the coil surfaces 111a and 112a of the power-supplying coils 111 and 112 may be different from each other. The coil surfaces 111a and 112a of the power-supplying coils 111 and 112 may be formed to correspond to a projected shape of a side face of the predetermined region A, or may be formed in accordance with factors such as the disposition of the other power-supplying coils 111, 112, and 115.

Each of the power-supplying coils 111 and 112 may be formed of plural power supplying sub coils. For example, in the power-supplying coil 111, a coil surface 111a which is trapezoidal on the whole may be formed by gathering power supplying sub coils 1111 which are identical or different in size. Alternatively, in the power-supplying coil 111, a coil surface 111a which is trapezoidal on the whole may be formed by gathering power supplying sub coils 1111 and power supplying sub coils 1112 which are different in shape from the power supplying sub coils 1111 and each of which is trapezoidal, for example.

The power-supplying coils 111 and 112 may be disposed so that the outer peripheries thereof partially overlap each other. With this arrangement, the magnetic field strength is easily uniformized by causing the outer peripheries of the power-supplying coils 111 and 112 with low magnetic field strength to overlap each other.

A coil surface 115a of the power-supplying coil 115 provided below the predetermined region A is sized and shaped to correspond to the size and shape of the bottom of the predetermined region A. For example, the coil surface 115a of the power-supplying coil 115 may be circular in shape to correspond to the size of the predetermined region A, or may have another shape. To be more specific, the coil surface 115a may be triangular as in a power-supplying coil 115A, the coil surface 115a may be quadrangular as in a power-supplying coil 115B, or the coil surface 115a may have another shape such as polygonal or elliptical. The shape of the coil surface 115a of the power-supplying coil 115 may correspond to the shape of the bottom of the predetermined region A, or may be determined in accordance with factors such as the disposition of the other power-supplying coils 111 and 112.

The number of the power-supplying coils 115 is one or more. When there are plural power-supplying coils 115, each of the power-supplying coils 115 may have a coil surface with a desired shape, as power supplying sub coils 1151 which are identical or different in size are gathered. Alternatively, a power-supplying coil 115 may be formed of an annular power supplying sub coil 1152 corresponding to the coil surface shape and power supplying sub coils 1151 provided on the inner circumferential side of the power supplying sub coil 1152. When a power-supplying coil 115 is formed by plural power supplying sub coils 1151 (1152), it is possible to finely adjust the magnetic field strength of a variable magnetic field at around the bottom portion of the predetermined region A, by each power supplying sub coil 1151 (1152).

(Power Supplying Device: Magnetic Field Formation Device: Oscillation Controller)

Figure 10:
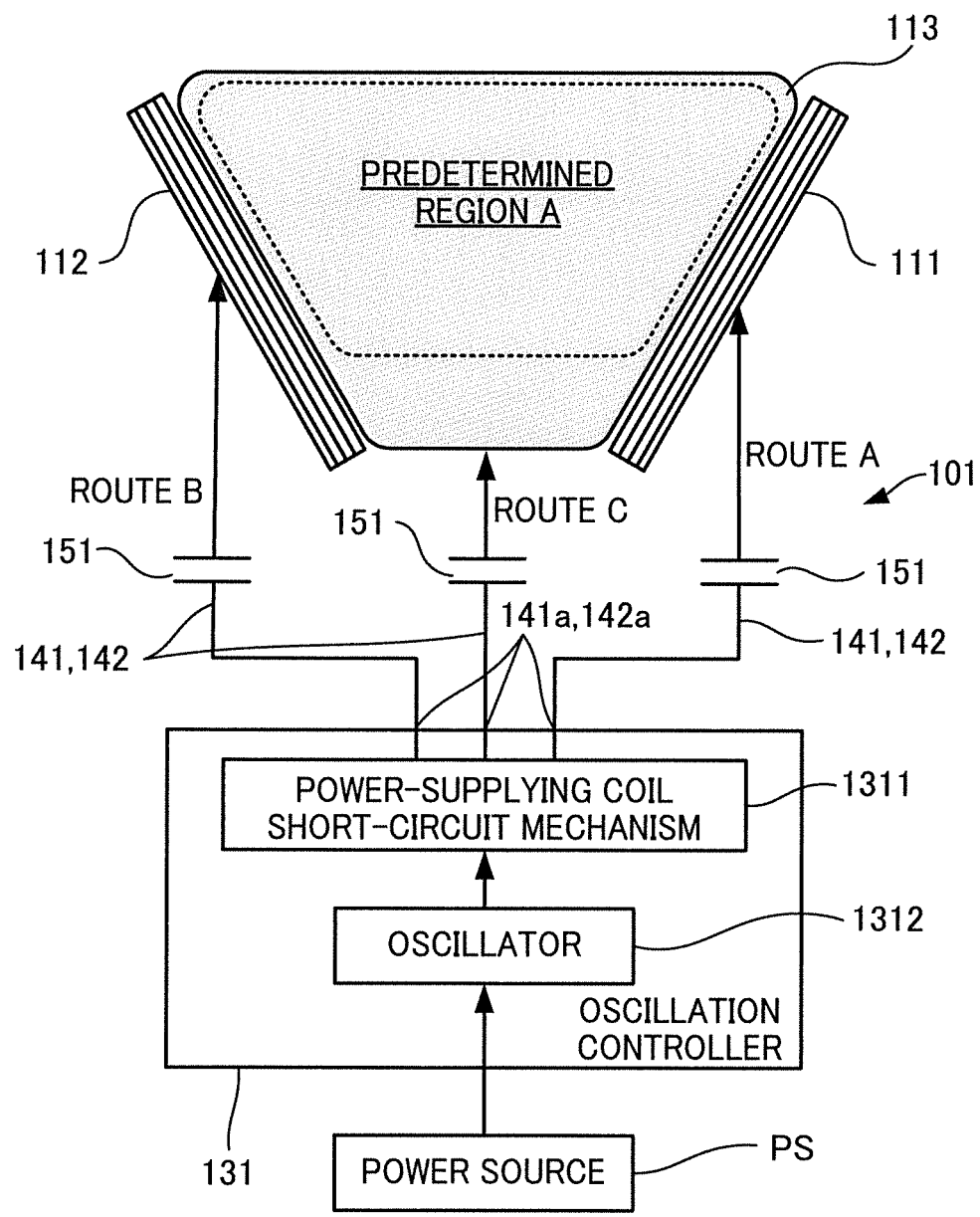
FIG. 10 is a block diagram of a magnetic field formation device.

As shown in FIG. 10, the magnetic field formation device 101 structured as described above includes the oscillation controller 131 (which is an example of a current output controller) connectable to an external power source PS. While a magnetic field formation device 101 including three power-supplying coils 111, 112, and 113 will be described below, the disclosure is not limited to this arrangement.

The oscillation controller 131 includes: a power-supplying coil short-circuit mechanism which causes each of the power-supplying coils 111, 112, and 113 to function as a power supplying resonator; and an output target switching mechanism which is configured to output a variable current to one of output targets which are at least one of and not all of the power-supplying coils 111, 112, and 113 and to be capable of switching the output target to which the variable current is output. The output target switching mechanism of the oscillation controller 131 is preferably arranged to repeatedly change plural magnetic field states each of which is a combination of the direction, density, and magnitude of magnetic lines of force in a variable magnetic field. In this case, the magnetic field strength of the variable magnetic field in the predetermined region A is uniformed by repeatedly changing plural magnetic field states each of which is a combination of the direction, density, and magnitude of magnetic lines of force in the variable magnetic field. With this arrangement, when, for example, the magnetic field formation device 101 is mounted on a power-supplying device, the power supply is possible without significant deterioration in the power receiving efficiency depending on the direction and position of the power-receiving device.

To be more specific, the oscillation controller 131 includes the oscillator 1312 configured to output a variable current and the power-supplying coil short-circuit mechanism 1313 which is capable of causing the end portions 141a and 142a of the first current path 141 and the second current path 142 of at least one of the power-supplying coils 111 and 112 to be short-circuited with each other. The power-supplying coil short-circuit mechanism 1313 is arranged to cause a variable current of the oscillator 1312 to flow in the power-supplying coils 111, 112, and 113 and stops the supply of the variable current to the power-supplying coil 111, 112, or 113 at the same time as that coil is short-circuited. The power-supplying coil short-circuit mechanism 1313 therefore has a function of switching the short-circuit of the power-supplying coils 111, 112, and 113 and a function as a current path switcher (output target switching mechanism) of switching the output target of the variable current of the oscillator 1312.

The magnetic field formation device 101 structured as above is able to cause at least one of the power-supplying coils 111, 112, and 113 to function as a power supplying resonator and change the distribution of the magnetic field strength of a variable magnetic field by sending a magnetic field to the power supplying resonator at a different angle. Furthermore, as the switching is repeated, a variable magnetic field with magnetic field strength which is uniformized in a variation amount can be formed at the predetermined region A. Furthermore, as at least one of the power-supplying coils 111, 112, and 113 functioning as a power supplying resonator resonates, the magnetic field strength of the variable magnetic field at the predetermined region A is enhanced.

(Power Supplying Device: Magnetic Field Formation Device: Oscillation Controller: Oscillator)

The oscillator 1312 is configured to receive a current outputted from the power source PS and is capable to outputting a variable current with any oscillating frequency. The oscillating frequency of the oscillator 1312 is preferably changeable to allow for the use of various types of magnetic field formation devices 101. Furthermore, each of the oscillating frequency, the voltage, and the current of the oscillator 1312 may be changeable in accordance with the specification of the power-supplying coil 111, 112, or 113 which is the output target.

While in the present embodiment the oscillator 1312 is indirectly connected to the current paths 141 and 142 via the power-supplying coil short-circuit mechanism 1313, the disclosure is not limited to this arrangement and the oscillator 1312 may be directly connected to the current paths 141 and 142. In this case, the variable current from the oscillator 1312 is concurrently supplied to all current paths 141 and 142, independently from the short-circuit operation by the current path switcher 1311. Alternatively, the power-supplying coil short-circuit mechanism 1313 may be connected to the power source PS and the oscillator 1312 may be provided on each of current paths connecting the power-supplying coil short-circuit mechanism 1313 with the respective power-supplying coils 111, 112, and 113. In this case, the power-supplying coil short-circuit mechanism 1313 is able to switch the power-supplying coil which is the output target of the variable current, by switching the output target of the current output from the power source PS between the three oscillators 1312 on the respective current paths.

(Power Supplying Device: Magnetic Field Formation Device: Oscillation Controller: Power-Supplying Coil Short-Circuit Mechanism)

As shown in FIG. 11, the power-supplying coil short-circuit mechanism 1313 includes: a switch mechanism which is configured to switchably output a variable current from the oscillator 1312 to each of the power-supplying coils 111, 112, and 113; and a short-circuit mechanism which is able to cause the end portions 141a and 142a of the first current path 141 and the second current path 142 of each of the power-supplying coils 111, 112, and 113 to short-circuit with each other.

The switch mechanism includes plural switches. Each of these switches is switchable between connection (on-state) and disconnection (off-state) of an input end and an output end. The input ends of all switches are connected to the oscillator 1312. Meanwhile, each output end is connectable to one of the end portions 141a and 142a of the first current path 141 and the second current path 142 of the power-supplying coils 111, 112, and 113 via a switch of the short-circuit mechanism. With this arrangement, the switch mechanism supplies a variable current from the oscillator 1312 to only one of the power-supplying coils 111, 112, and 113, which is connected to a switch in the on-state.

The short-circuit mechanism includes switches which correspond to the respective power-supplying coils 111, 112, and 113. Each of these switches is switchable between short-circuit (on-state) and disconnection (off-state) of a first terminal and a second terminal. The first terminal of each switch is connected to the end portion 141a of the first current path 141 of each of the power-supplying coils 111, 112, and 113. The second terminal of each switch is connected to the end portion 142*a* of the second current path 142 of each of the power-supplying coils 111, 112, and 113. With this arrangement, the switches of the short-circuit mechanism are able to cause the end portions 141*a* and 142*a* of the first current path 141 and the second current path 142 of each of the power-supplying coils 111, 112, and 113 to be short-circuited or disconnected, by switching the first terminal and the second terminal between short-circuited (on-state) and disconnected (off-state). While in the present embodiment the end portions 141*a* and 142*a* of the first current path 141 and the second current path 142 are short-circuited by the short-circuit mechanism, the disclosure is not limited to this arrangement. The end portions 141*a* and 142*a* may be connected to the GND to be short-circuited.

The switches of the above-described short-circuit mechanism are arranged to operate in sync with the switch mechanism. To be more specific, the switch mechanism stops the output of a variable current from the oscillator 1312 to the power-supplying coils 111, 112, and 113 for which the end portions 141*a* and 142*a* of the first current path 141 and the second current path 142 are short-circuited by a switch of the short-circuit mechanism, whereas the switch mechanism outputs the variable current from the oscillator 1312 to the power-supplying coils 111, 112, and 113 for which the end portions 141*a* and 142*a* of the first current path 141 and the second current path 142 are disconnected.

The power-supplying coil short-circuit mechanism 1313 includes a short-circuit control mechanism. The short-circuit control mechanism is able to switch each switch between the on-state and the off-state. For example, there are: a short-circuit pattern 1 in which the end portions 141*a* and 142*a* of the first current path 141 and the second current path 142 of the power-supplying coil 111 are short-circuited; a short-circuit pattern 2 in which the end portions 141*a* and 142*a* of the power-supplying coil 112 are short-circuited; a short-circuit pattern 3 in which the end portions 141*a* and 142*a* of the power-supplying coil 113 are short-circuited; a short-circuit pattern 4 in which the end portions 141*a* and 142*a* of the power-supplying coils 111 and 112 are short-circuited; a short-circuit pattern 5 in which the end portions 141*a* and 142*a* of the power-supplying coils 112 and 113 are short-circuited; and a short-circuit pattern 6 in which the end portions 141*a* and 142*a* of the power-supplying coils 111 and 113 are short-circuited. The short-circuit control mechanism is able to switch a combination selected from these short-circuit patterns 1 to 6 at any timing. As described above, in the present embodiment, there are six output targets as an output target of the variable current from the oscillator 1312, and the output target of the variable current is switchable by the short-circuit control mechanism.

In addition to the above, the short-circuit control mechanism of the power-supplying coil short-circuit mechanism 1313 has a function of executing a process of short-circuiting the end portions 141*a* and 142*a* with a predetermined combination of a timing and a duration. With this arrangement, the short-circuit control mechanism is able to easily generate a variable magnetic field with predetermined magnetic field strength in consideration of heat generation and power consumption, by adjusting the timing and duration of the connection process.

To be more specific, the short-circuit control mechanism is able to select one of plural short-circuit times (time 1 to time n), and a suitable short-circuit time is selected in consideration of the use and state of the magnetic field formation device 101. The short-circuit control mechanism is able to determine a timing to execute the short-circuit operation between the end portions 141*a* and 142*a*, by means of plural short-circuit patterns. To be more specific, there are "every 1 pattern" with which the short-circuit operation is executed each time one of the short-circuit patterns 1 to 6 is completed, "every 2 patterns" with which the short-circuit operation is executed each time two of the short-circuit patterns 1 to 6 are completed, and so on. As one of these options is selected, various short-circuit operations are executable at a desired timing.

(Power Supplying Device: Magnetic Field Formation Device: Modification of Oscillation Controller: Power-Supplying Coil Short-Circuit Mechanism and Current Path Switcher)

Figure 12:
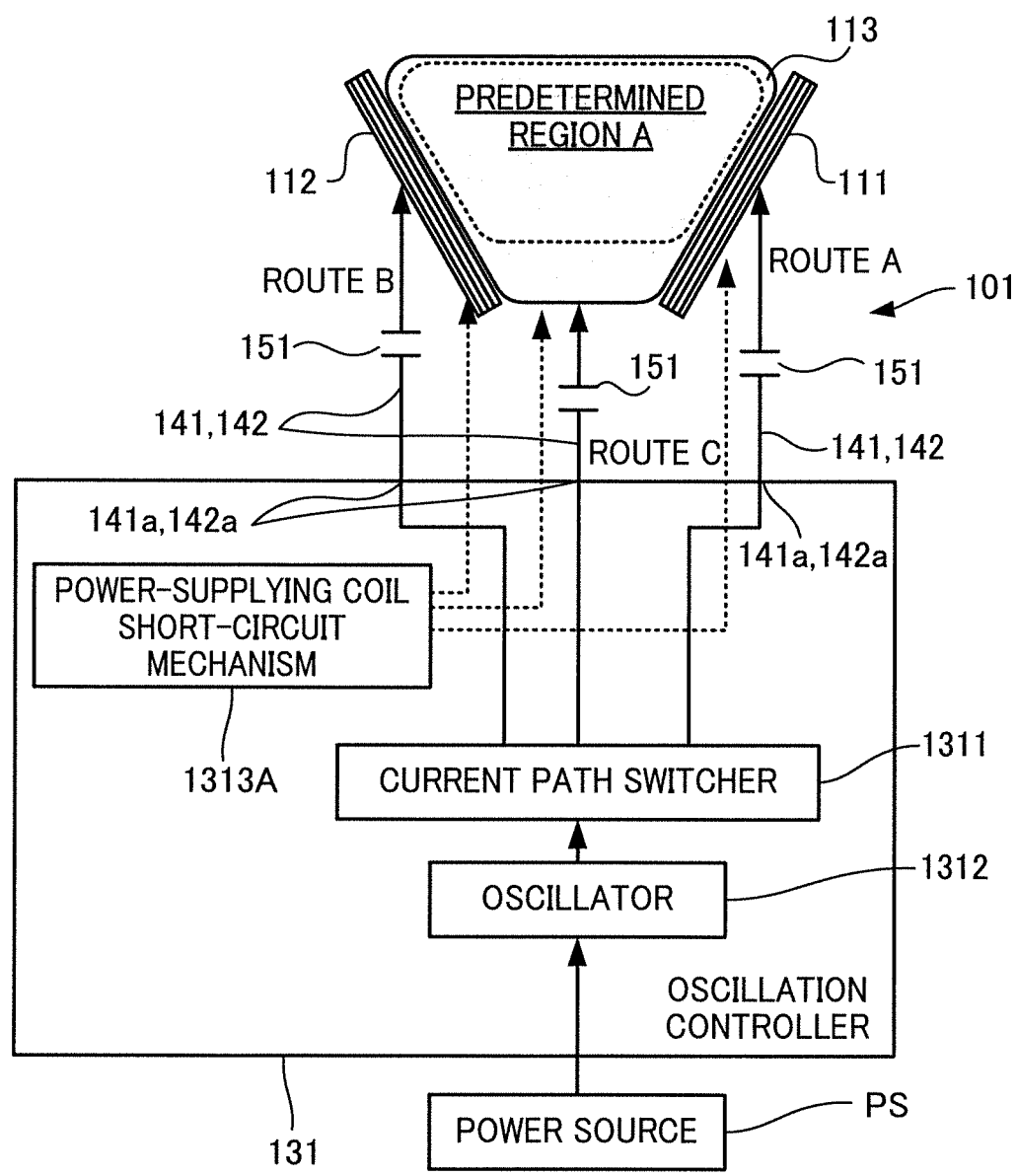
FIG. 12 is a block diagram of a magnetic field formation device.

While in the oscillation controller 131 above the power-supplying coil short-circuit mechanism 1313 executes a part of the function of the current path switcher, the disclosure is not limited to this arrangement. As shown in FIG. 12, a power-supplying coil short-circuit mechanism 1313A and a current path switcher 1311 may be independently provided. Control is easily done in this case, because control for short-circuiting is separated from control for current switching.

To be more specific, the oscillation controller 131 includes the power-supplying coil short-circuit mechanism 1313A including only the short-circuit mechanism, the oscillator 1312, and the current path switcher 1311 which performs switching to supply the variable current of the oscillator 1312 to at least one of and not all of the power-supplying coils 111, 112, and 113.

(Power Supplying Device: Magnetic Field Formation Device: Oscillation Controller: Current Path Switcher)

The current path switcher 1311 includes a switch mechanism which is configured to switchably output the variable current of the oscillator 1312 to each of the power-supplying coils 111, 112, and 113. The switch mechanism includes plural switches. Each of these switches is switchable between connection (on-state) and disconnection (off-state) of an input end and an output end. The input ends of all switches are connected to the oscillator 1312. Meanwhile, the output ends are connected to the respective power-supplying coils 111, 112, and 113. With this arrangement, the switch mechanism supplies a variable current from the oscillator 1312 only to one of the power-supplying coils 111, 112, and 113, which is connected to a switch in the on-state.

As shown in FIG. 13, the current path switcher 1311 includes a switch control mechanism. The switch control mechanism is able to switch each switch of the switch mechanism between the on-state and the off-state. For example, provided that a route through which the variable current is supplied to the power-supplying coil 111 is a route A, a route through which the variable current is supplied to the power-supplying coil 112 is a route B, and a route through which the variable current is supplied to the power-supplying coil 113 is a route C, there are six connection patterns 1 to 6.

To be more specific, there are (1) a connection pattern 1 with which the variable current is supplied only to the power-supplying coil 111 by using only the route A; (2) a connection pattern 2 with which the variable current is supplied only to the power-supplying coil 112 by using only the route B; (3) a connection pattern 3 with which the variable current is supplied only to the power-supplying coil 113 by using only the route C; (4) a connection pattern 4 with which the variable current is supplied to the power-supplying coils 111 and 112 by using the route A and the route B; (5) a connection pattern 5 with which the variable current is supplied to the power-supplying coils 112 and 113 by using the route B and the route C; and (6) a connection pattern 6 with which the variable current is supplied to the power-supplying coils 111 and 113 by using the route A and the route C. The switch control mechanism is able to switch a combination selected from these connection patterns 1 to 6 at any timing.

In addition to the above, the switch control mechanism of the current path switcher 1311 has a function of executing a stop process of not supplying the variable current to any of the power-supplying coils 111, 112, and 113, with a predetermined combination of a timing and a duration. With this arrangement, the switch control mechanism is able to easily generate a variable magnetic field with predetermined magnetic field strength in consideration of heat generation and power consumption, by adjusting the timing and duration of the stop process.

To be more specific, the switch control mechanism is able to perform a pause operation (stop process) of stopping the power supply to all of the power-supplying coils 111, 112, and 113 by turning off all switches of the switch mechanism. In the pause operation, a pause time is selectable from plural pause times (time 1 to time n), and a suitable pause time is selected in consideration of the use and state of the magnetic field formation device 101.

In addition to the above, the switch control mechanism is able to determine a timing to execute the pause operation based on plural pause patterns. To be more specific, there are "every 1 pattern" with which the pause operation is executed each time one of the connection patterns 1 to 6 is completed, "every 2 patterns" with which the pause operation is executed each time two of the connection patterns 1 to 6 are completed, and so on. As one of these options is selected, various pause operations are executable at a desired timing.

For example, the current path switcher 1311 is able to perform a powering operation in which a route A connection state with the connection pattern 1, the pause operation, a route B connection state with the connection pattern 2, the pause operation, a route C connection state with the connection pattern 3, and the pause operation are repeated in order. Furthermore, for example, the current path switcher 1311 is able to perform a powering operation in which the route A connection state with the connection pattern 1, the route B connection state with the connection pattern 2, the route C connection state with the connection pattern 3, and the pause operation are repeated in order.

The current path switcher 1311 may be constituted by a circuit having a programmability such as a microcomputer and an operation of switching the variable current may executed by software, or may be constituted by a combination of ICs and the switching operation may be executed by hardware.

(Specific Example of Power Supplying Device)

Figure 14:
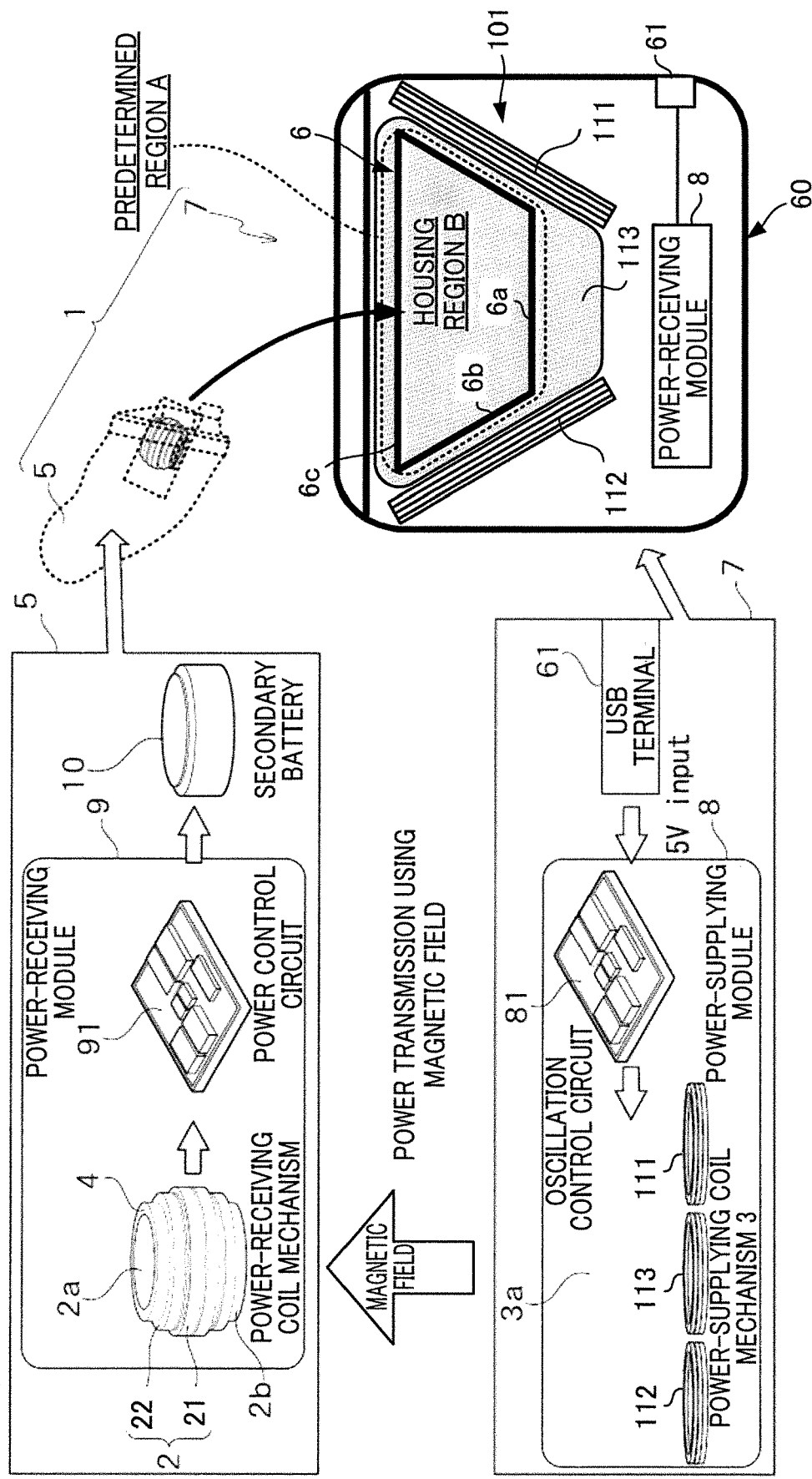
FIG. 14 is a block diagram of a power receiving/supplying device.

As shown in FIG. 14, the charger 7 (power-supplying device) including the magnetic field formation device 101 and the housing cup 6 structured as above constitutes a power receiving/supplying device 1 or a power receiving/supplying system, together with the driving device 5 electrically charged by the charger 7. To put it differently, the power receiving/supplying device 1 includes the driving device 5 including the power-receiving coil mechanism 2 receiving power by a magnetic field and the charger 7 supplying power to the driving device 5 by wireless transmission. In the power receiving/supplying device 1, the charger 7 and the driving device 5 may be treated in combination.

The magnetic field formation device 101 is provided in a casing of the charging case 60 in which the housing cup 6 is provided. In the magnetic field formation device 101, any of the power-supplying coils 111, 112, and 113 functions as a power-supplying coil whereas the remaining power-supplying coils 111, 112, and 113 function as a power-supplying resonator. A power-supplying coil mechanism 3 including the power-supplying coils 111, 112, and 113 is connected to an oscillation control circuit 81 which is an IC chip in which the oscillation controller 131 outputting a variable current is embodied.

The oscillation control circuit 81 and the power-supplying coil mechanism 3 are combined as a power-supplying module 8 in order to improve the handleability. The oscillation control circuit 81 is connected to a USB terminal 61. The USB terminal 61 is connectable to an unillustrated USB cable of an external device such as a personal computer provided outside the charger 7, so that 5V DC power can be supplied from the external device to the oscillation control circuit 81. Instead of the USB terminal 61, the charger 7 may be connected to a home AC power cord, and DC power converted from AC power by a rectifying circuit or a converter may be suppliable to the oscillation control circuit 81.

(Driving Device)

The driving device 5 charged and operated by the above-described charger 7 encompasses a handheld device which can be carried on a hand and a human-wearable device which can be worn on a human body. Specific examples of the driving device 5 include a portable computer (a laptop PC, a note PC, a tablet PC, or the like), a headset, a camera, an audio visual device (a portable music player, an IC recorder, a portable DVD player, or the like), a calculator (such as a pocket computer and an electronic calculator), a game console, a computer peripheral (a portable printer, a portable scanner, a portable modem, or the like), a dedicated information device (an electronic dictionary, an electronic notebook, an electronic book, a portable data terminal, or the like), a portable communication terminal, a voice communication terminal (a portable phone, a PHS, a satellite phone, a third party radio system, an amateur radio, a specified low power radio, a personal radio, a citizen radio, or the like), a data communication terminal (a portable phone, a PHS (a feature phone and a smart phone), a pager, or the like), a broadcasting receiver (a television receiver and a radio), a portable radio, a portable television receiver, a one-seg receiver, another type of device (a wristwatch and a pocket watch), a hearing aid, a handheld GPS, a security buzzer, a flashlight/pen light, a battery pack, and the like. Examples of the above hearing aid include an ear-hook hearing aid, an ear hole fitting hearing aid, and a glasses-type hearing aid. In addition to the above-described mobile devices, examples of the driving device 5 include a robot, a drone or the like, which autonomously moves in a space (box or a room).

(Driving Device: Power-Receiving Coil Mechanism)

The driving device 5 includes the power-receiving coil mechanism 2 which is configured to receive power by a magnetic field. In addition to the power-receiving coil mechanism 2, the driving device 5 includes: a power control circuit 91 to which power is supplied from the power-receiving coil mechanism 2; and a magnetic member 4. The power-receiving coil mechanism 2, the power control circuit 91, and the magnetic member 4 are integrated as a power-receiving module 9. The power-receiving module 9 is connected to a secondary battery 10.

The power-receiving coil mechanism 2 is configured to receive power in such a way that magnetic field resonance is caused by a variable magnetic field in the housing region B (predetermined region A). To be more specific, the power-receiving coil mechanism 2 includes a power-receiving coil 21 and a power-receiving resonator 22 provided on the inner circumferential side of the power-receiving coil 21. The "magnetic field resonance" indicates a resonance phenomenon of synchronization at a resonance frequency of a variable magnetic field. Examples of the types of coils used in the power-receiving coil 21 and the power-receiving resonator 22 include: a spiral type, a solenoid type, and a loop type. In regard to the positional relation between the power-receiving coil 21 and the power-receiving resonator 22, the power-receiving coil 21 may be provided on the inner circumferential side or the outer circumference side of the power-receiving resonator 22, or the power-receiving coil 21 and the power-receiving resonator 22 may be provided not to overlap each other in the radial direction.

The driving device 5 includes the magnetic member 4 provided at the power-receiving coil mechanism 2. The magnetic member 4 increases the magnetic field strength by increasing the mutual inductance of the power-receiving coil mechanism 2 and increasing the magnetic flux density. As the magnetic field strength of the power-receiving coil mechanism 2 is increased by the magnetic member 4, the charging characteristic is maintained to be high in the power-receiving coil mechanism 2, and power at least at a desired level is receivable with an improved degree of freedom in the layout of the power-receiving coil mechanism 2. The power-receiving coil mechanism 2 preferably includes the magnetic member 4 but may not include the magnetic member 4.

The magnetic member 4 is provided on the inner circumferential side of the power-receiving coil mechanism 2. While the positional relation between the power-receiving coil mechanism 2 and the magnetic member 4 in the axial direction, i.e., the positional relation when viewed in the direction orthogonal to the axial direction is not particularly limited, these members are preferably provided so that the power-receiving coil mechanism 2 is provided at an intermediate portion between one end side and the other end side of the magnetic member 4. This "intermediate portion" between one end side and the other end side of the magnetic member 4 indicates a part of a region sandwiched between the one end and the other end, excluding the one end and the other end.

The positional relation between the power-receiving coil mechanism 2 and the magnetic member 4 in the axial direction is further preferably arranged so that the power-receiving coil mechanism 2 is provided at a central portion between one end side and the other end side of the magnetic member 4. The positional relation between the power-receiving coil mechanism 2 and the magnetic member 4 in the axial direction is preferably arranged such that the charging characteristic of the magnetic member 4 is not significantly different between a case where the coil surface 2a of the power-receiving coil mechanism 2 on one side faces a magnetic field generating surface 3a of the power-supplying coil mechanism 3 and a case where the coil surface 2b of the power-receiving coil mechanism 2 on the other side faces the magnetic field generating surface 3a.

The power-receiving resonator 22 of the power-receiving coil mechanism 2 is provided so that the power-receiving coil 21 is disposed on the outer circumference side. To be more specific, the power-receiving coil mechanism 2 is arranged such that the power-receiving resonator 22 is provided between the power-receiving coil 21 on the outermost circumferential side and the magnetic member 4 on the innermost circumferential side. While the positional relation between the power-receiving resonator 22 and the power-receiving coil 21 in the axial direction is not particularly limited, these members are preferably provided so that the power-receiving coil 21 is provided at an intermediate portion between one end side and the other end side of the power-receiving resonator 22. The positional relation between the power-receiving resonator 22 and the power-receiving coil 21 in the axial direction is further preferably arranged so that the power-receiving coil 21 is provided at a central portion between one end side and the other end side of the power-receiving resonator 22.

The magnetic member 4 is made of resin in which magnetic powder is dispersed. The resin used for the magnetic member 4 may be thermosetting resin or thermoplastic resin, and is not particularly limited. Examples of the thermosetting resin include epoxy resin, phenol resin, melamine resin, vinyl ester resin, cyano ester resin, maleimide resin, and silicon resin. Examples of the thermoplastic resin include acrylic resin, vinyl acetate based resin, and poly vinyl alcohol based resin. The present example adopts a resin whose main component is epoxy resin.

Further, soft magnetic powder is used as the magnetic powder dispersed in the resin. Examples of the soft magnetic powder include pure Fe, Fe—Si, Fe—Al—Si (sendust), Fe—Ni (permalloy), soft ferrites, Fe-base amorphous, Co-base amorphous, and Fe—Co (permendur); however, is not particularly limited. The shape of the magnetic member 4 is suitably determined, too.

(Driving Device: Power Control Circuit)

The power control circuit 91 is mounted on a circuit substrate.

Figure 15:
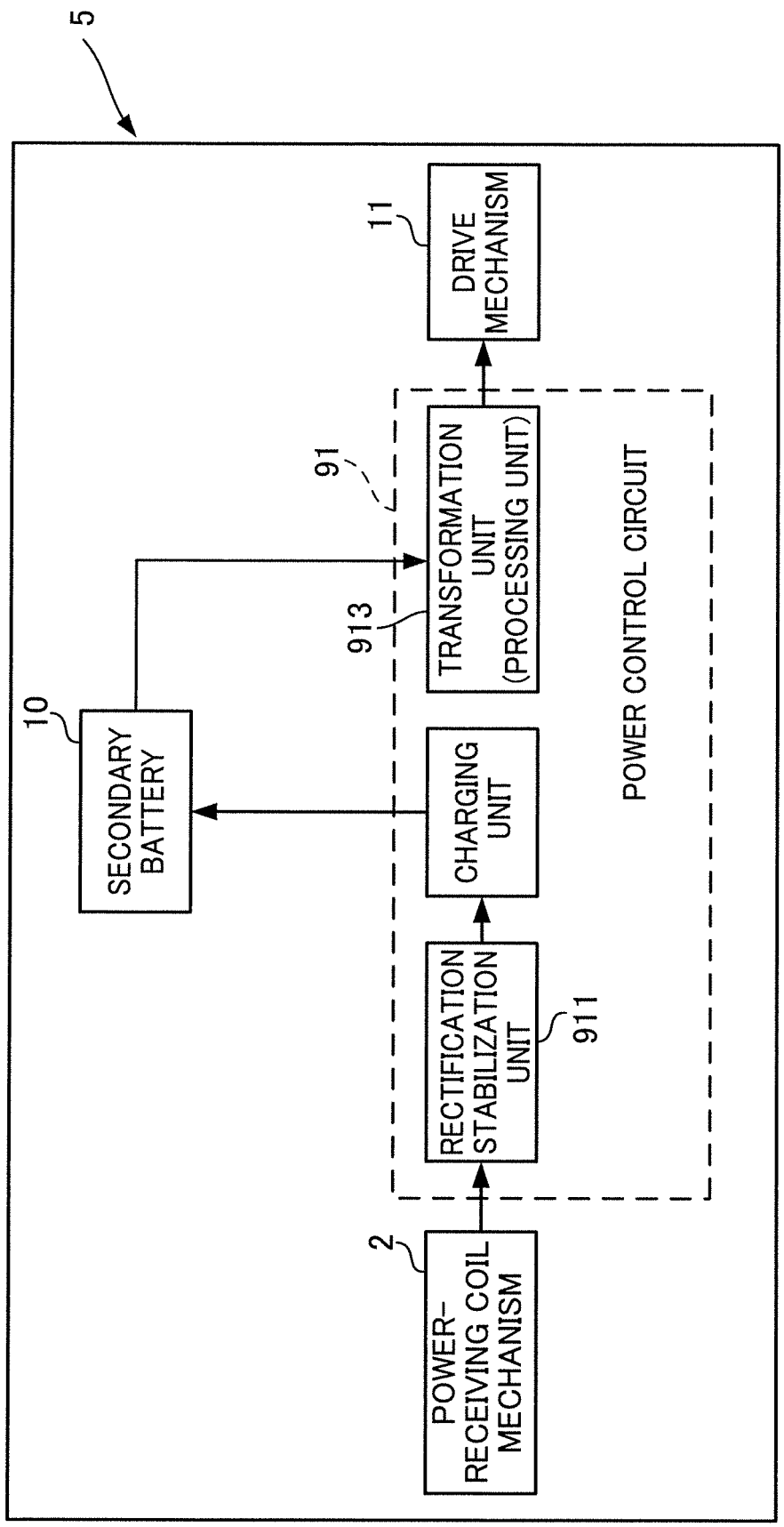
FIG. 15 is a block diagram of a driving device.

As shown in FIG. 15, the power control circuit 91 has a function of controlling the charging of the secondary battery 10. The power control circuit 91 may be a circuit further having a function of controlling the discharging.

To be more specific, the power control circuit 91 includes a rectification stabilization unit 911 which is configured to output DC power by rectifying AC power supplied from the outside via the power-receiving coil mechanism 2 outputting the DC power, a charging unit 912 configured to supply the DC power outputted from the rectification stabilization unit 911 to the secondary battery 10 at a charging voltage, and a transformation unit 913 configured to execute a signal process. The transformation unit 913 is connected to a driving mechanism 11 which is driven by the charged power of the secondary battery 10.

The rectification stabilization unit 911 is a rectification-stabilization IC, for example. The rectification-stabilization IC is an IC in which functions such as full bridge synchronous rectification, voltage conditioning and wireless power control, and protection from a voltage, current, or temperature anomaly are integrated into one chip. The rectification stabilization unit 911 may not be provided when the power outputted from the power-receiving coil mechanism 2 is DC power.

The charging unit 912 is an IC (charging circuit) for a constant current/constant voltage linear charger, and has functions such as a function of notifying that the charging current has been reduced to a predetermined setting value, a function of ending the charging using a timer, a function of stabilizing the charging current by means of thermal feedback, and a function of limiting the chip temperature in a high-power mode or in high ambient temperatures.

The transformation unit 913 is a transformer circuit which functions as a transformation unit performing signal processing of converting the charged power of the secondary battery 10 to the driving power for the driving mechanism 11 and outputting the converted power. As the transformation unit 913, a linear regulator may be employed for voltage dropping, or a switching regulator or a charge pump may be employed for voltage boosting and voltage dropping. An example of each regulator is one adopting a semiconductor elements so the current is switched on and off at a high speed.

(Driving Device: Power Control Circuit with High-Capacitance Capacitor)

Figure 16:
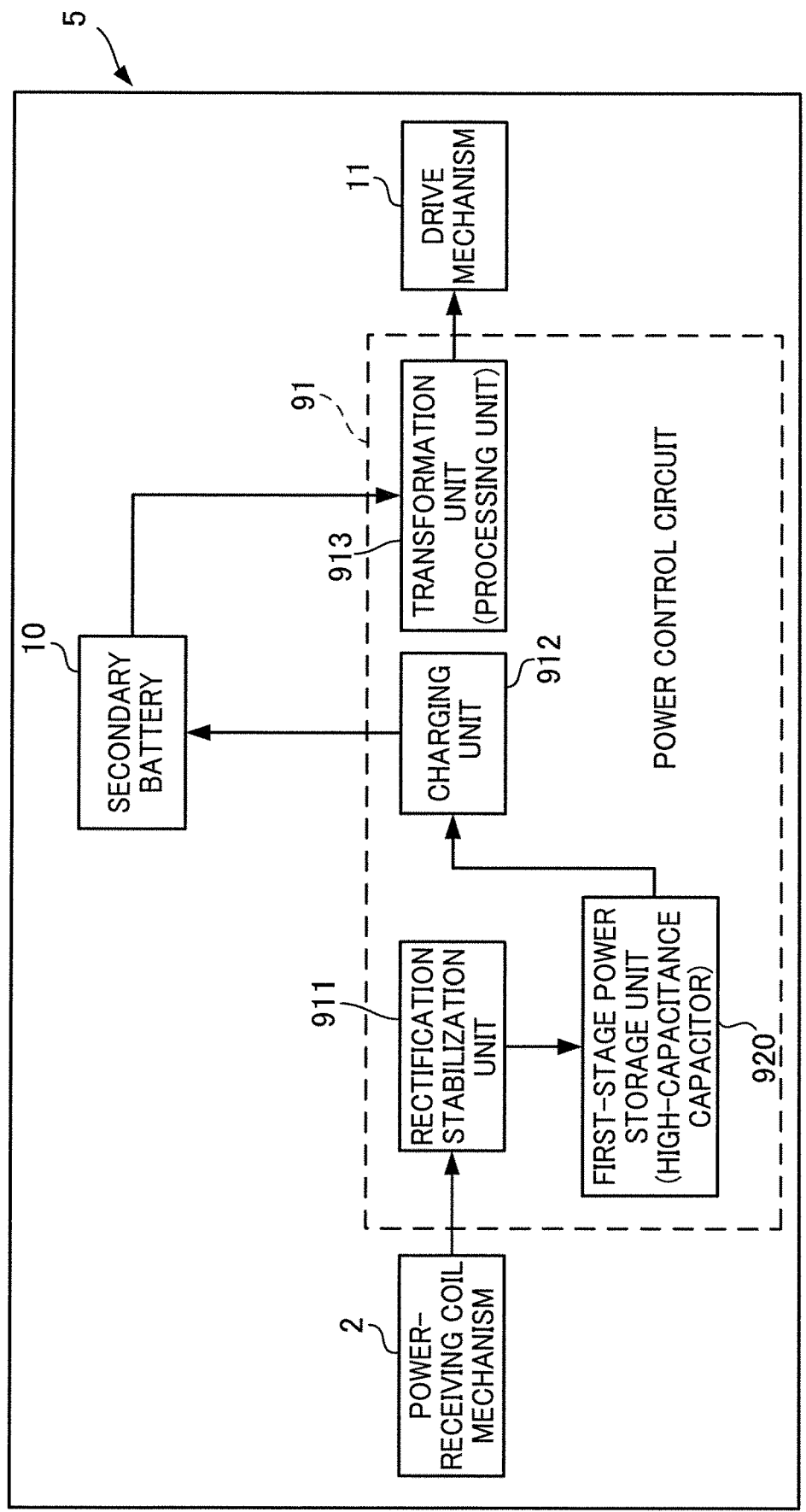
FIG. 16 is a block diagram of a driving device.
Figure 17:
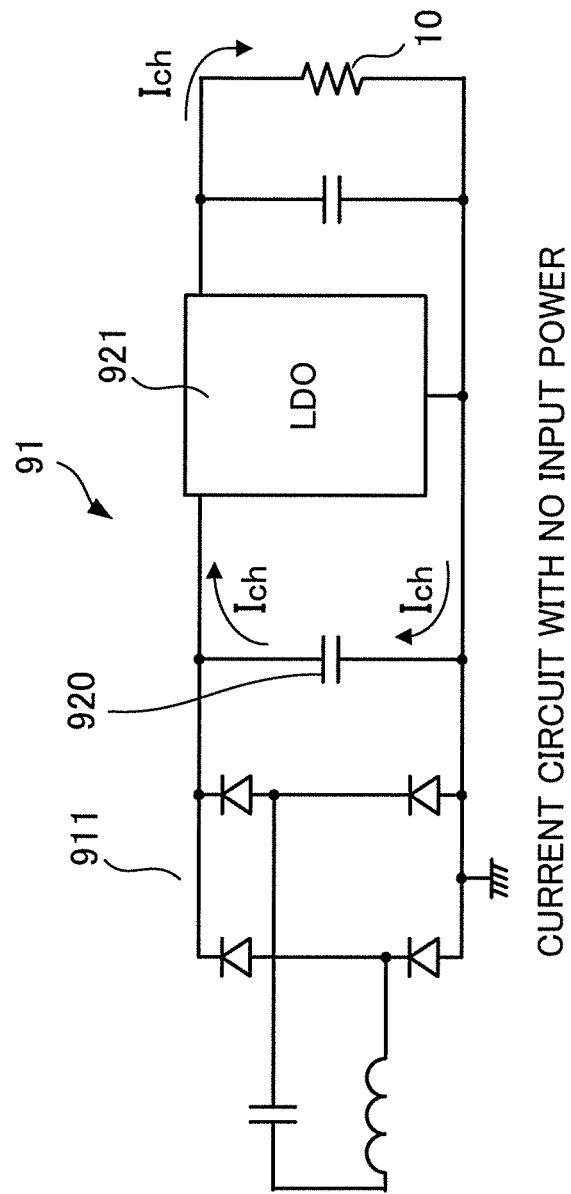
FIG. 17 is a block diagram of a driving device.

As shown in FIG. 16 and FIG. 17, the power control circuit 91 may include a high-capacitance capacitor as a first-stage power storage unit 920. The first-stage power storage unit 920 has a capacity of discharging at a voltage equal to or higher than the minimum operating voltage of an electric part on a subsequent stage, and is preferably provided in cases where a received voltage varies. The "electric part" encompasses not only a secondary battery and an electronic circuit substrate but also all driving devices driven by supplied power. The "minimum operating voltage" indicates the minimum voltage with which an electric part is properly driven. For example, the minimum operating voltage of a secondary battery is the minimum voltage with which a charging IC of the secondary battery is properly driven.

The first-stage power storage unit 920 is particularly preferable when switching of conduction to the power-supplying coils 111, 112, and 113 is performed by the power-supplying coil short-circuit mechanism 1313 or the current path switcher 1311. To be more specific, the driving device 5 (power-receiving device) including the power control circuit 91 may be configured to receive power by a variable magnetic field generated at the predetermined region A by the magnetic field formation device 101, and may include: the power-receiving coil mechanism 2 (power-receiving mechanism) configured to receive power by the variable magnetic field; and the first-stage power storage unit 920 (high-capacitance capacitor) having a capacity of being charged by a current received by the power-receiving coil mechanism 2 and discharging at least at the minimum operating voltage of the secondary battery 10, etc. (electric part) on a subsequent stage while the current path switcher 1311 is performing the switching of the output target.

The driving device 5 may include: the power-receiving coil mechanism 2 (power-receiving device) configured to receive power by a variable magnetic field; and a capacitor having a capacity of being charged by a current received by the power-receiving coil mechanism 2 and discharging at least at the minimum operating voltage of the secondary battery 10, etc. (electric part) on a subsequent stage while the current path switcher 1311 is performing the stop process.

According to the arrangement above, even when an induced current cannot be obtained from the power-receiving coil mechanism 2 on account of the switching process or the stop process performed for the power-supplying coils 111, 112, and 113, the charging unit 912 or the like is stably driven because the first-stage power storage unit 920 performs the discharge at least at the minimum operating voltage of the charging unit 912 or the like.

The first-stage power storage unit 920 (high-capacitance capacitor) may have a capacity of discharging at least at the minimum operating voltage of an electric part on a subsequent stage during the stop process in which the current path switcher 1311 does not supply a variable current to any of the power-supplying coils 111, 112, and 113, in addition to the period during which the switching of the output target is being performed by the power-supplying coil short-circuit mechanism 1313 or the current path switcher 1311. According to this arrangement, in addition to the period during which the switching of the output target is being performed by the current path switcher 1311, even when an induced current cannot be obtained from a power-receiving coil due to the stop process for the power-supplying coil and the power supplying resonator, the electric part is stably driven as the first-stage power storage unit 920 performs the discharge at least at the minimum operating voltage of the electric part.

(Driving Device: Driving Mechanism)

Examples of the driving mechanism 11 include a mechanism in which a component converting electric power to kinetic energy such as a speaker and a motor is incorporated, alight emitting mechanism or an illumination mechanism in which a component converting electric power to optical energy such as an LED light source and a laser light source is incorporated, and a microcomputer. Apart from these mechanisms, any types of mechanism driven by electric power may be used as the driving mechanism 11. The power-receiving coil mechanism 2 is configured to correspond to wireless power supply with which power supply is carried out in a mechanically contactless state. Examples of the wireless power supply include electromagnetic induction and magnetic field resonance (magnetic resonance).

(Driving Device: Secondary Battery)

As the secondary battery 10, any type of batteries which are chargeable and rechargeable can be used. Examples of the secondary battery 10 include a lead storage battery, a valve-regulated lead storage battery, a lithium ion battery, a lithium ion polymer battery, a lithium iron phosphate ion battery, a lithium-sulfur battery, a lithium titanate battery, a nickel-cadmium storage battery, a nickel-hydrogen rechargeable battery, a nickel-iron battery, a nickel-lithium battery, a nickel-zinc battery, a rechargeable alkali battery, a sodium-sulfur battery, a redox flow battery, a zinc-bromine flow battery, a silicon battery, and a Silver-Zinc battery.

The charger 7 (power-supplying device) may be provided with a display which displays the charging state of the secondary battery 10 of the driving device 5. The charging state indicates at least one of errors such as heating, overcharging, and over-discharging, a charging amount, and the life such as the charging cycle number and the replacement timing of the secondary battery 10. A dryer for drying the driving device 5 may be included, and a sterilizer for sterilizing the driving device 5 may be included.

Embodiment 2

Figure 18:
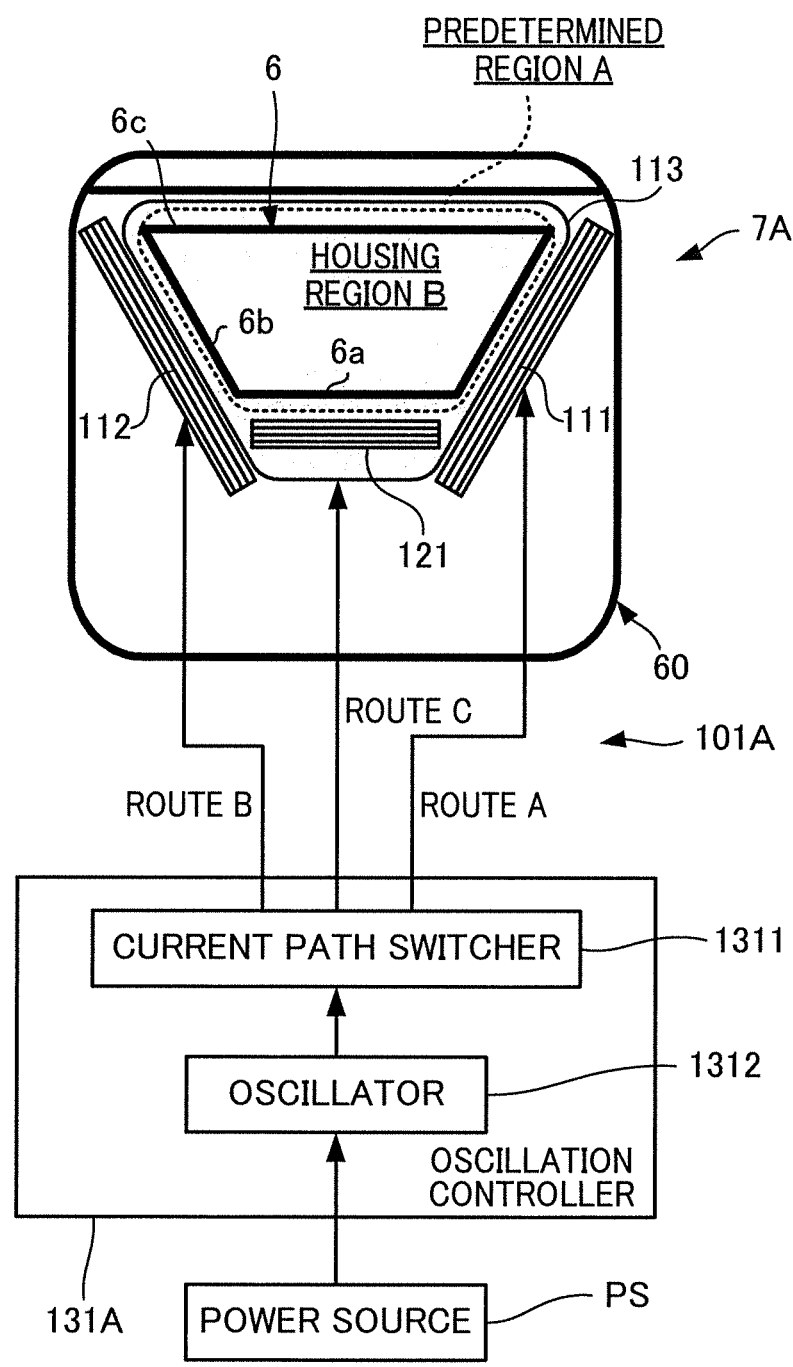
FIG. 18 is a block diagram of a charger.

The following will describe Embodiment 2 of the present invention with reference to FIG. 18. Members identical with those of Embodiment 1 will be denoted by the same reference numerals and the descriptions thereof are omitted. Furthermore, in FIG. 18, a resonance capacitor provided on a current path is not shown.

A charger 7A which is a power-supplying device of Embodiment 2 is arranged such that at least one power supplying resonator 121 is added to the charger 7 of Embodiment 1. To be more specific, the charger 7A includes the housing cup 6 having the housing region B and a magnetic field formation device 101A configured to generate a variable magnetic field at the predetermined region A including the housing region B. The magnetic field formation device 101A is configured to generate a variable magnetic field at the predetermined region A.

Figure 19:
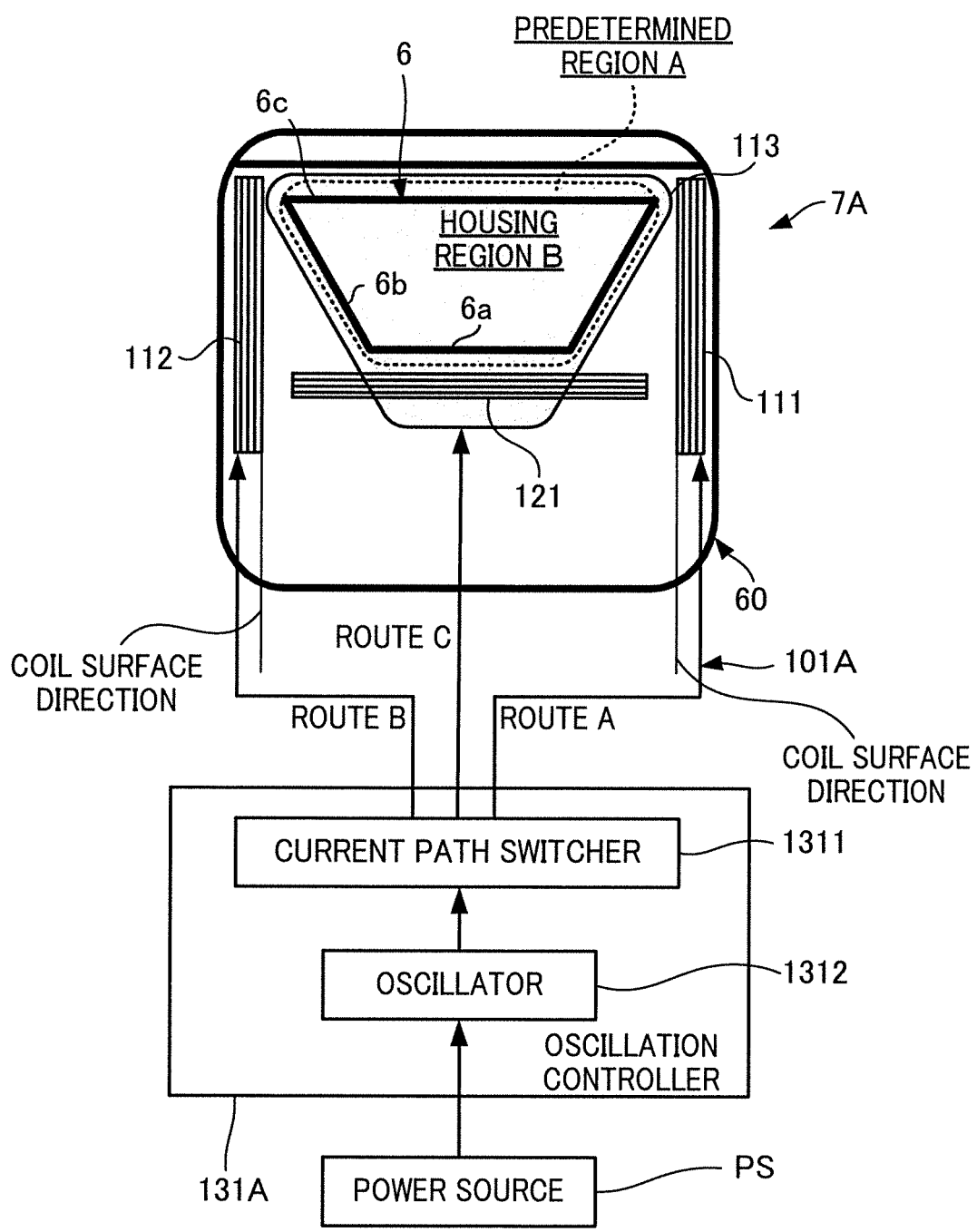
FIG. 19 is a block diagram of a charger.

The magnetic field formation device 101A includes at least one power supplying resonator 121 configured to generate a variable magnetic field and power-supplying coils 111, 112, and 113 configured to generate an induced current in the power supplying resonator 121. All of the power-supplying coils 111, 112, and 113 and all of the at least one power supplying resonator 121 are provided so that coil surfaces 111a, 112a, 113a, and 121a oppose the predetermined region A including the housing region B surrounded by the bottom surface portion 6a and the side face portion 6b of the housing cup 6, and at least one of the power-supplying coils 111, 112, and 113 is provided to have a coil surface direction intersecting with the coil surface direction of the remaining one or more of the power-supplying coils 111, 112, and 113. Alternatively, as shown in FIG. 19, at least one of the power-supplying coils 111, 112, and 113 may be provided to have a coil surface direction parallel to the coil surface direction of the remaining one or more of the power-supplying coils 111, 112, and 113.

In the magnetic field formation device 101A structured as above, a variable magnetic field with high magnetic field strength or low magnetic field strength can be formed at a part of the predetermined region A by the variable magnetic fields of the power-supplying coils 111, 112, and 113 and the variable magnetic field of the power supplying resonator 121, based on the positional relation between the power-supplying coils 111, 112, and 113 and the power supplying resonator 121. This is achieved by adjusting the angles, locations, etc. of the coil surfaces 111a, 112a, and 113a of the power-supplying coils 111, 112, and 113. In this way, a magnetic field which is partially a variable magnetic field with high or low magnetic field strength can be formed at the predetermined region A.

To be more specific, in the magnetic field formation device 101A, the power supplying resonator 121 is provided to oppose the bottom surface portion 6a of the horizontally-provided housing cup 6. To be more specific, the power-supplying coils 111, 112, and 113 are provided at the side face portion 6b of the housing cup 6 to oppose one another and to be at equal intervals in the circumferential direction. The power-supplying coils 111, 112, and 113 supply magnetic fields to the power supplying resonator 121 at a central part when viewed from the upper surface of the charger 7, so that the power supplying resonator 121 generates a variable magnetic field at the housing region B.

(Magnetic Field Formation Device: Power Supplying Resonator)

The power supplying resonator 121 is of a spiral type, a solenoid type, or a loop type, for example, and is a coil in which the ends of the coil are directly connected (short-circuited) to each other or indirectly connected (short-circuited) to each other by a GND or the like. The power supplying resonator 121 is provided so that a coil surface 121a opposes the lower bottom of the predetermined region A. With this arrangement, when an induced current is supplied, the power supplying resonator 121 generates a variable magnetic field at the predetermined region A opposing the coil surface 121a and generates a variable magnetic field at a region opposite to the predetermined region A over the power supplying resonator 121.

The coil surface 121a of the power supplying resonator 121 is sized and shaped to correspond to the size and shape of the bottom of the predetermined region A. For example, the coil surface 121a of the power supplying resonator 121 may be circular in shape to correspond to the size of the predetermined region A, or may have another shape. The shape of the coil surface 121a of the power supplying resonator 121 may correspond to the shape of the bottom of the predetermined region A, or may be determined in accordance with factors such as the disposition of the other power-supplying coils 111 and 112.

The number of the power supplying resonator 121 is one or more. When there are plural power supplying resonators 121, each of the power supplying resonators 121 may have a coil surface with a desired shape, as resonator sub coils which are identical or different in size are gathered. When the power supplying resonator 121 is formed by plural resonator sub coils, it is possible to finely adjust the magnetic field strength of a variable magnetic field generated by each resonator sub coil. While in Embodiment 2 the power supplying resonator 121 is provided to oppose the bottom surface portion 6a of the housing cup 6, the disclosure is not limited to this arrangement and the power supplying resonator 121 may be provided to oppose the side face portion 6b of the housing cup 6.

(Magnetic Field Formation Device: Oscillation Controller)

The magnetic field formation device 101A structured as above includes an oscillation controller 131A. The oscillation controller 131A includes the oscillator 1312 configured to output a variable current and the current path switcher 1311 which is configured to switch the variable current of the oscillator 1312 to be supplied to not all of and at least one of the power-supplying coils 111, 112, and 113. To put it differently, the current path switcher 1311 sets at least one of and not all of the power-supplying coils 111, 112, and 113 as the output target of the variable current of the oscillator 1312, and is able to switch the output target. With this, the oscillation controller 131 is able to change the distribution of the magnetic field strength of a variable magnetic field, as the power-supplying coils 111, 112, and 113 send a magnetic field to the power supplying resonator 121 at a different angle. Furthermore, as the switching is repeated, a variable magnetic field with uniform magnetic field strength is formed at the predetermined region A as compared to cases where the positional relation between the power-supplying coils 111, 112, and 113 and the power supplying resonator 121 is fixed. Furthermore, as the power supplying resonator 121 resonates on account of the variable magnetic field of each of the power-supplying coils 111, 112, and 113, the magnetic field strength of the variable magnetic field at the predetermined region A is enhanced. The arrangements and operations other than the above are identical with those in Embodiment 1.

Although the above descriptions have been provided with regard to the characteristic parts so as to understand the invention more easily, the invention is not limited to the embodiment as described above and can be applied to the other embodiments and the applicable scope should be construed as broadly as possible. Furthermore, the terms and phraseology used in the specification have been used to correctly illustrate the present invention, not to limit it. In addition, it will be understood by those skilled in the art that the other structures, systems, methods and the like included in the spirit of the present invention can be easily derived from the spirit of the invention described in the specification. Accordingly, it should be considered that the present invention covers equivalent structures thereof without departing from the spirit and scope of the invention as defined in the following claims. In addition, it is required to sufficiently refer to the documents that have been already disclosed, so as to fully understand the objects and effects of the present invention.

REFERENCE SIGNS LIST 1 power receiving/supplying device
2 power-receiving coil mechanism 3 power-supplying coil mechanism
4 magnetic member
5 driving device
6 housing cup
7 charger
7A charger
8 power-supplying module
9 power-receiving module
10 secondary battery
21 power-receiving coil
22 power-receiving resonator
111 power-supplying coil
112 power-supplying coil
131 oscillation controller
131A oscillation controller
1111 power supplying sub coil
1112 power supplying sub coil
1311 current path switcher
1312 oscillator
A predetermined region
B housing region

The invention claimed is:

1. A power-supplying device comprising:
a housing cup which includes a bottom surface portion on which at least one driving device including a power-receiving device is placed and a side face portion extending outward from a peripheral edge portion of the bottom surface portion, the housing cup being formed so that an upper peripheral edge portion of the side face portion is an opening portion; and
a magnetic field formation device configured to generate a variable magnetic field at a housing region surrounded by the bottom surface portion and the side face portion to allow the power-receiving device to receive power irrespective of the direction and position of the power-receiving device,
the magnetic field formation device including:
at least one power supplying resonator configured to generate the variable magnetic field; and
power-supplying coils configured to generate an induced current in the at least one power supplying resonator,
the at least one power supplying resonator and the power-supplying coils being disposed so that coil surfaces oppose a predetermined region including the housing region surrounded by the bottom surface portion and the side face portion of the housing cup, and
the magnetic field formation device outputting a variable current to one of output targets which are at least one of and not all of the power-supplying coils and being capable of repeatedly switching the output target to which the variable current is output.

2. The power-supplying device according to claim 1, wherein, the magnetic field formation device repeatedly changes plural magnetic field states each of which is a combination of a direction, density, and magnitude of magnetic lines of force in the variable magnetic field.

3. The power-supplying device according to claim 1, wherein, the magnetic field formation device includes:
the power-supplying coils each of which generates a variable magnetic field as a variable current is supplied to each of the power-supplying coils via a first current path on one coil end side and a second current path on the other coil end side;
a resonance capacitor which is provided on at least one of the first current path and the second current path; and
a power-supplying coil short-circuit mechanism which is capable of causing at least one of the power-supplying coils to function as a power supplying resonator by short-circuiting end portions of the first current path and the second current path.

4. The power-supplying device according to claim 1, wherein, a stop process of not outputting the variable current to any of the power-supplying coils is executed with a predetermined combination of a timing and a duration.

5. The power-supplying device according to claim 1, further comprising a display which is configured to display a charging state of a battery provided in the driving device.

6. The power-supplying device according to claim 1, further comprising a drier configured to dry the driving device.

7. The power-supplying device according to claim 1, further comprising a sterilizer configured to sterilize the driving device.

8. A power receiving/supplying device comprising:
the power-supplying device according to claim 1; and
a power-receiving device which is housed in the housing region of the housing cup of the power-supplying device and is configured to receive power by the variable magnetic field.

* * * * *